US012593992B2

(12) United States Patent
Terazawa

(10) Patent No.: US 12,593,992 B2
(45) Date of Patent: Apr. 7, 2026

(54) SPHYGMOMANOMETER, PERSONAL AUTHENTICATION METHOD ON A SPHYGMOMANOMETER, AND COMPUTER-READABLE RECORDING MEDIUM

(71) Applicant: OMRON HEALTHCARE Co., Ltd., Muko (JP)

(72) Inventor: Sho Terazawa, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 398 days.

(21) Appl. No.: 18/136,032

(22) Filed: Apr. 18, 2023

(65) Prior Publication Data

US 2023/0255500 A1 Aug. 17, 2023

Related U.S. Application Data

(63) Continuation of application No. PCT/JP2021/042449, filed on Nov. 18, 2021.

(30) Foreign Application Priority Data

Nov. 30, 2020 (JP) ................................. 2020-198364

(51) Int. Cl.
| | |
|---|---|
| *A61B 5/021* | (2006.01) |
| *A61B 5/022* | (2006.01) |
| *A61B 5/117* | (2016.01) |

(52) U.S. Cl.
CPC .......... *A61B 5/02108* (2013.01); *A61B 5/022* (2013.01); *A61B 5/117* (2013.01)

(58) Field of Classification Search
None
See application file for complete search history.

(56) References Cited

U.S. PATENT DOCUMENTS

| | | | | |
|---|---|---|---|---|
| 5,653,241 A | * | 8/1997 | Harada | G16H 40/63 |
| | | | | 600/495 |
| 6,171,254 B1 | * | 1/2001 | Skelton | A61B 5/022 |
| | | | | 600/490 |

(Continued)

FOREIGN PATENT DOCUMENTS

| | | |
|---|---|---|
| CN | 102293652 A | 12/2011 |
| CN | 102772202 A | 11/2012 |

(Continued)

OTHER PUBLICATIONS

Dec. 28, 2021 International Search Report issued in International Patent Application No. PCT/JP2021/042449.

(Continued)

*Primary Examiner* — Aurelie H Tu
(74) *Attorney, Agent, or Firm* — Oliff PLC

(57) ABSTRACT

A sphygmomanometer of the present invention includes a cuff for compressing a site to be measured of a subject, and measures a blood pressure by observing a pressure of the cuff. The sphygmomanometer includes a feature acquisition unit that acquires feature information regarding a pressure change pattern of a subject to be authenticated. The pressure change pattern rises while increasing its increase rate with a lapse of time from a start of pressurization in a pressurization process of a cuff. The sphygmomanometer further includes an authentication unit that compares the acquired feature information with registered feature information regarding a user registered in advance, and performs personal authentication on the subject.

10 Claims, 12 Drawing Sheets

(56)                        References Cited

U.S. PATENT DOCUMENTS

| | | | | |
|---|---|---|---|---|
| 2011/0152650 A1* | 6/2011 | Donehoo | ............. | A61B 5/0225 |
| | | | | 600/490 |
| 2017/0011210 A1* | 1/2017 | Cheong | ................. | A61B 5/681 |
| 2017/0245769 A1 | 8/2017 | Niehaus et al. | | |
| 2019/0365259 A1 | 12/2019 | Nishikawa et al. | | |
| 2024/0306995 A1* | 9/2024 | Zheng | ................. | A61B 5/0245 |

FOREIGN PATENT DOCUMENTS

| | | |
|---|---|---|
| CN | 103228204 A | 7/2013 |
| CN | 107692993 A | 2/2018 |
| JP | H06-142065 A | 5/1994 |
| JP | 2003-299624 A | 10/2003 |
| JP | 2010-110380 A | 5/2010 |
| JP | 2015-70969 A | 4/2015 |
| JP | 2016-214519 A | 12/2016 |
| JP | 2018-161382 A | 10/2018 |
| JP | 2019-115618 A | 7/2019 |

OTHER PUBLICATIONS

Oct. 7, 2025 Office Action issued in Brazilian Patent Application No. BR112023006815-0.
Jul. 31, 2025 Office Action issued in Chinese Patent Application No. 202180077411.9.

* cited by examiner

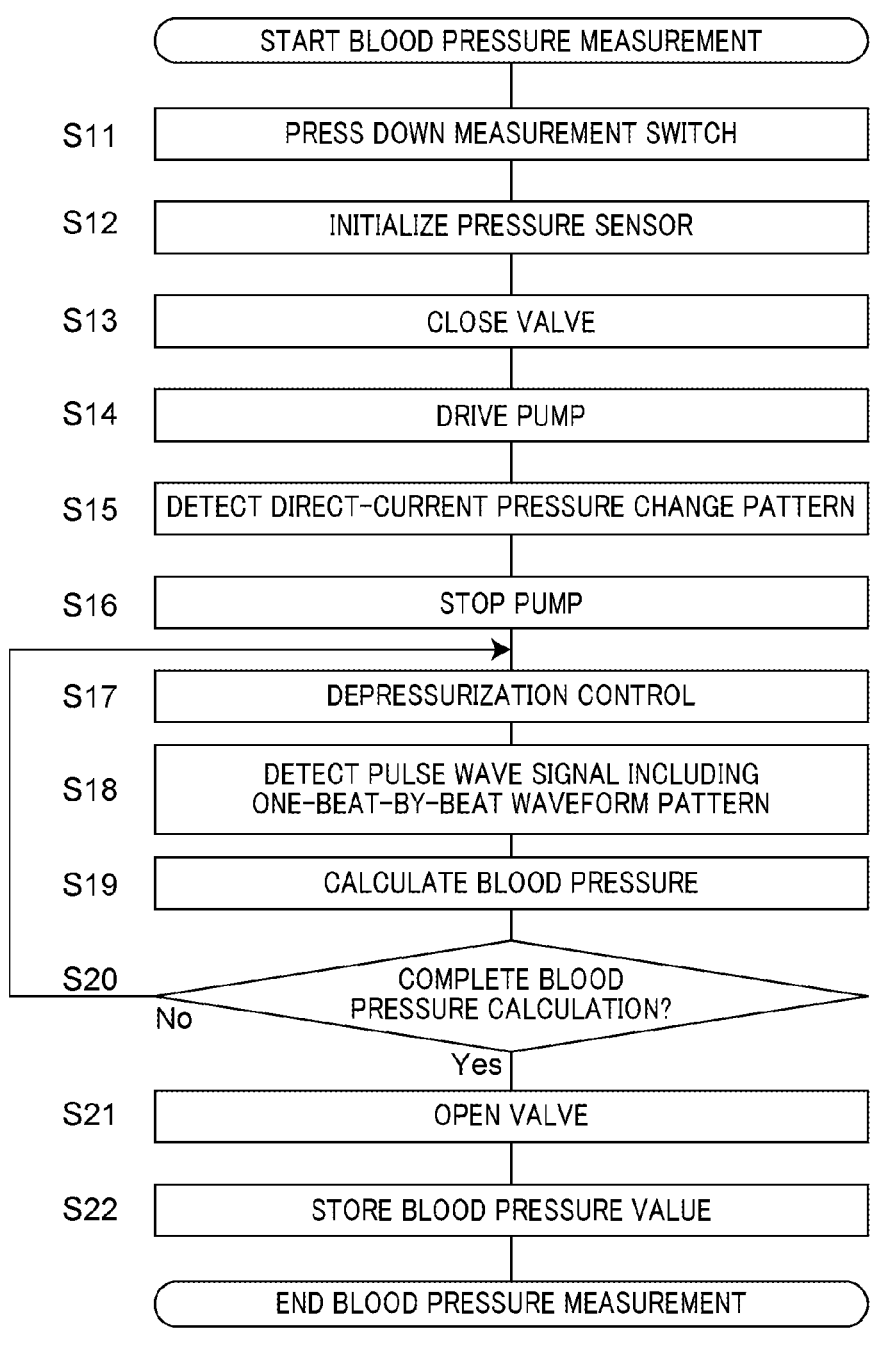

START BLOOD PRESSURE MEASUREMENT

S11    PRESS DOWN MEASUREMENT SWITCH

S12    INITIALIZE PRESSURE SENSOR

S13    CLOSE VALVE

S14    DRIVE PUMP

S15    DETECT DIRECT-CURRENT PRESSURE CHANGE PATTERN

S16    STOP PUMP

S17    DEPRESSURIZATION CONTROL

S18    DETECT PULSE WAVE SIGNAL INCLUDING ONE-BEAT-BY-BEAT WAVEFORM PATTERN

S19    CALCULATE BLOOD PRESSURE

S20    COMPLETE BLOOD PRESSURE CALCULATION?
No
Yes

S21    OPEN VALVE

S22    STORE BLOOD PRESSURE VALUE

END BLOOD PRESSURE MEASUREMENT

START REGISTRATION MODE

S101   REGISTER NEW USER REGISTRATION NUMBER
       ACCORDING TO SELECTION OF USER

S102   BLOOD PRESSURE MEASUREMENT

S103   ACQUIRE FEATURE INFORMATION

S104   ASSOCIATE FEATURE INFORMATION WITH
       USER REGISTRATION NUMBER,
       AND STORE FEATURE INFORMATION

END REGISTRATION MODE

USER U1 : MUSCULAR AND THICK ARM

USER U2 : MUSCULAR AND THIN ARM

USER U3 : FAT AND THICK ARM

USER U4 : FAT AND THIN ARM

Fig. 11

SPHYGMOMANOMETER, PERSONAL AUTHENTICATION METHOD ON A SPHYGMOMANOMETER, AND COMPUTER-READABLE RECORDING MEDIUM

CROSS-REFERENCE TO RELATED APPLICATIONS

This application claims benefit of priority to Japanese Patent Application 2020-198364, filed Nov. 30, 2020, the entire content of which is incorporated herein by reference.

TECHNICAL FIELD

The present invention relates to a sphygmomanometer, and more particularly to a sphygmomanometer having a personal authentication function. Furthermore, the present invention relates to a personal authentication method on a sphygmomanometer. Furthermore, the present invention relates to a computer-readable recording medium storing a program for causing a computer to execute such a personal authentication method on a sphygmomanometer.

BACKGROUND ART

When a subject measures a blood pressure using a sphygmomanometer, it may be desired to perform personal authentication (confirmation of being a registered user himself/herself) on the subject in order to associate the subject with a blood pressure value to be measured. Conventionally, as a method of performing personal authentication by a sphygmomanometer, for example, as disclosed in Patent Document 1 (JP 2010-110380 A) and Patent Document 2 (JP H06-142065 A), a method using a pattern of level change of Korotkoff sound is known. Furthermore, as disclosed in Patent Document 3 (JP 2003-299624 A), there is known a remote diagnosis support system that extracts a feature parameter from an electrocardiographic signal transmitted by a user to a server, performs personal authentication using a neural network classification method or the like, and then performs diagnosis.

SUMMARY OF THE INVENTION

However, since the Korotkoff sound and the electrocardiographic signal have a large variation for each measurement, there is a problem that it is difficult to perform accurate authentication. Furthermore, recently, as a sphygmomanometer, a sphygmomanometer that measures a blood pressure by, for example, an oscillometric method by observing a pressure (internal pressure) of a cuff has been widely used. In such a sphygmomanometer of a type that measures the blood pressure by observing the pressure of the cuff, if personal authentication is performed by the Korotkoff sound or an electrocardiographic signal, there is a problem that extra components (for example, a sound detecting device such as a microphone, an electrocardiographic electrode, and the like) that are not used for pressure observation need to be provided.

Therefore, an object of the present invention is to provide a sphygmomanometer that measures a blood pressure by observing a pressure of a cuff, the sphygmomanometer being capable of performing personal authentication with high accuracy with a simple configuration. Furthermore, another object of the present invention is to provide a personal authentication method on such a sphygmomanometer. Furthermore, another object of the present invention is to provide a computer-readable recording medium storing a program for causing a computer to execute such a personal authentication method.

In order to achieve the object, a sphygmomanometer of the present disclosure is a sphygmomanometer including a cuff configured to compress a site to be measured of a subject and measuring a blood pressure by observing a pressure of the cuff, the sphygmomanometer comprising:

a pressure control unit that performs control to supply a fluid to the cuff to pressurize the cuff or discharge the fluid from the cuff to depressurize the cuff;

a pressure detection unit that detects a pressure of the cuff;

a blood pressure calculation unit that calculates a blood pressure based on an output of the pressure detection unit;

a feature acquisition unit that acquires, for a subject to be authenticated, feature information on a pressure change pattern of the cuff with a lapse of time from a start of pressurization in a pressurization process of the cuff; and an authentication unit that compares the acquired feature information with registered feature information on a user registered in advance, and performs personal authentication on the subject.

In the present specification, the "pressure of the cuff" means a pressure in the cuff (typically, a fluid bag contained in the cuff). Hereinafter, the "pressure of the cuff" is appropriately abbreviated as a "cuff pressure".

The "pressure change pattern" means a pattern in which the pressure of the cuff changes with the lapse of time from the start of pressurization in the pressurization process of the cuff. A pressure fluctuation component due to a pulse wave indicated by the site to be measured is superimposed on the pressure of the cuff in addition to a smoothly monotonically increasing component (direct-current component).

To "perform personal authentication" means to determine whether or not the subject to be authenticated is a user (the person himself/herself) registered in advance. In the present specification, it is determined whether or not the subject is a user registered in advance according to whether or not the feature information regarding the pressure change pattern of the subject matches the registered feature information regarding the user registered in advance. Note that the "user registered in advance" may be singular or plural.

The "registered feature information" is typically feature information acquired by the feature acquisition unit and stored in a storage unit in advance before the personal authentication is performed.

In another aspect, a personal authentication method of the present disclosure is a personal authentication method on a sphygmomanometer including a cuff configured to compress a site to be measured of a subject and measuring a blood pressure by observing a pressure of the cuff, the sphygmomanometer including:

a pressure control unit that performs control to supply a fluid to the cuff to pressurize the cuff or discharge the fluid from the cuff to depressurize the cuff;

a pressure detection unit that detects a pressure of the cuff; and a blood pressure calculation unit that calculates a blood pressure based on an output of the pressure detection unit, the personal authentication method comprising:

acquiring, for a subject to be authenticated, feature information on a pressure change pattern of the cuff with a lapse of time from a start of pressurization in a pressurization process of the cuff; and comparing the acquired feature information with regis-
tered feature information on a user registered in
advance, and performs personal authentication on the
subject.

In yet another aspect, a computer-readable recording
medium according to the present disclosure is a non-transi-
torily computer-readable recording medium storing a pro-
gram for causing a computer to execute the above personal
authentication method on a sphygmomanometer.

BRIEF DESCRIPTION OF DRAWINGS

FIG. 1 is a diagram illustrating a block configuration of a
sphygmomanometer according to an embodiment of the
present invention.

FIG. 3 is a diagram illustrating a flow of blood pressure
measurement by the sphygmomanometer.

Figure 6:
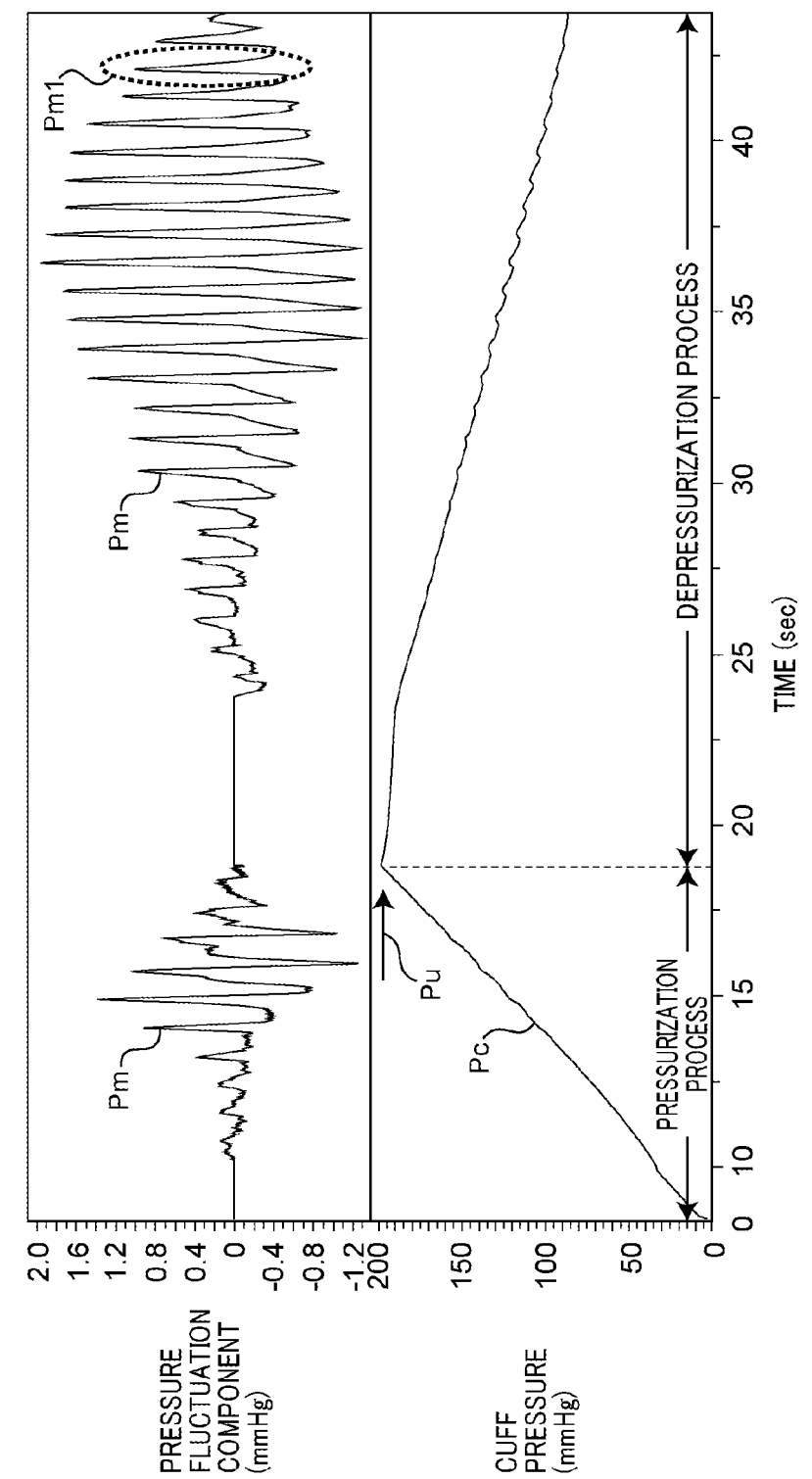

Lower section of FIG. 6 is a diagram illustrating a change
in cuff pressure with a lapse of time from the start of
pressurization. Upper section of FIG. 6 is a diagram illus-
trating a pressure fluctuation component (pulse wave signal)
of the cuff pressure obtained with the lapse of time from the
start of pressurization.

Figures 7A, 7B:
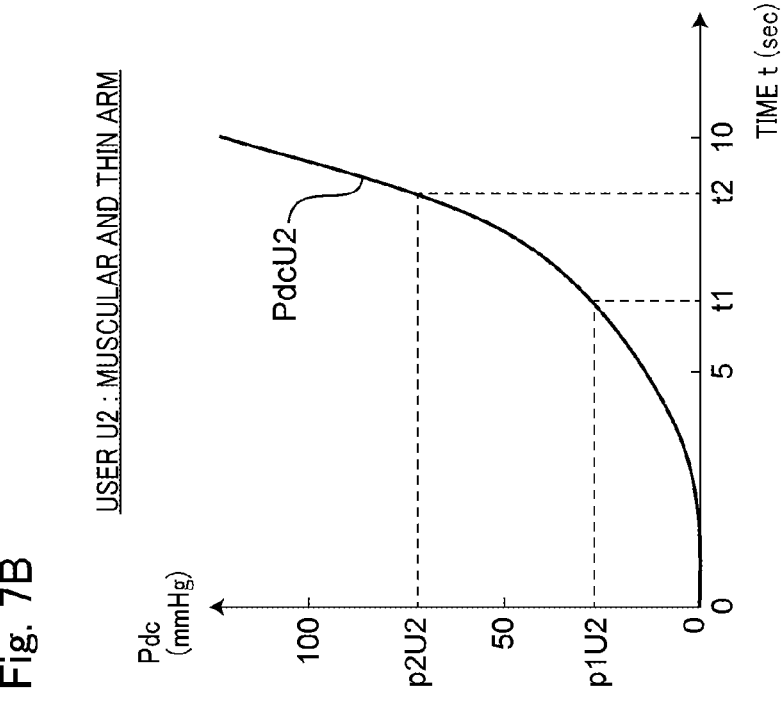

FIG. 7A is a diagram illustrating a direct-current pressure
change pattern with the lapse of time from the start of
pressurization for a muscular and thick arm user.

FIG. 7B is a diagram illustrating a direct-current pressure
change pattern with the lapse of time from the start of
pressurization for a muscular and thin arm user.

Figures 8A, 8B:
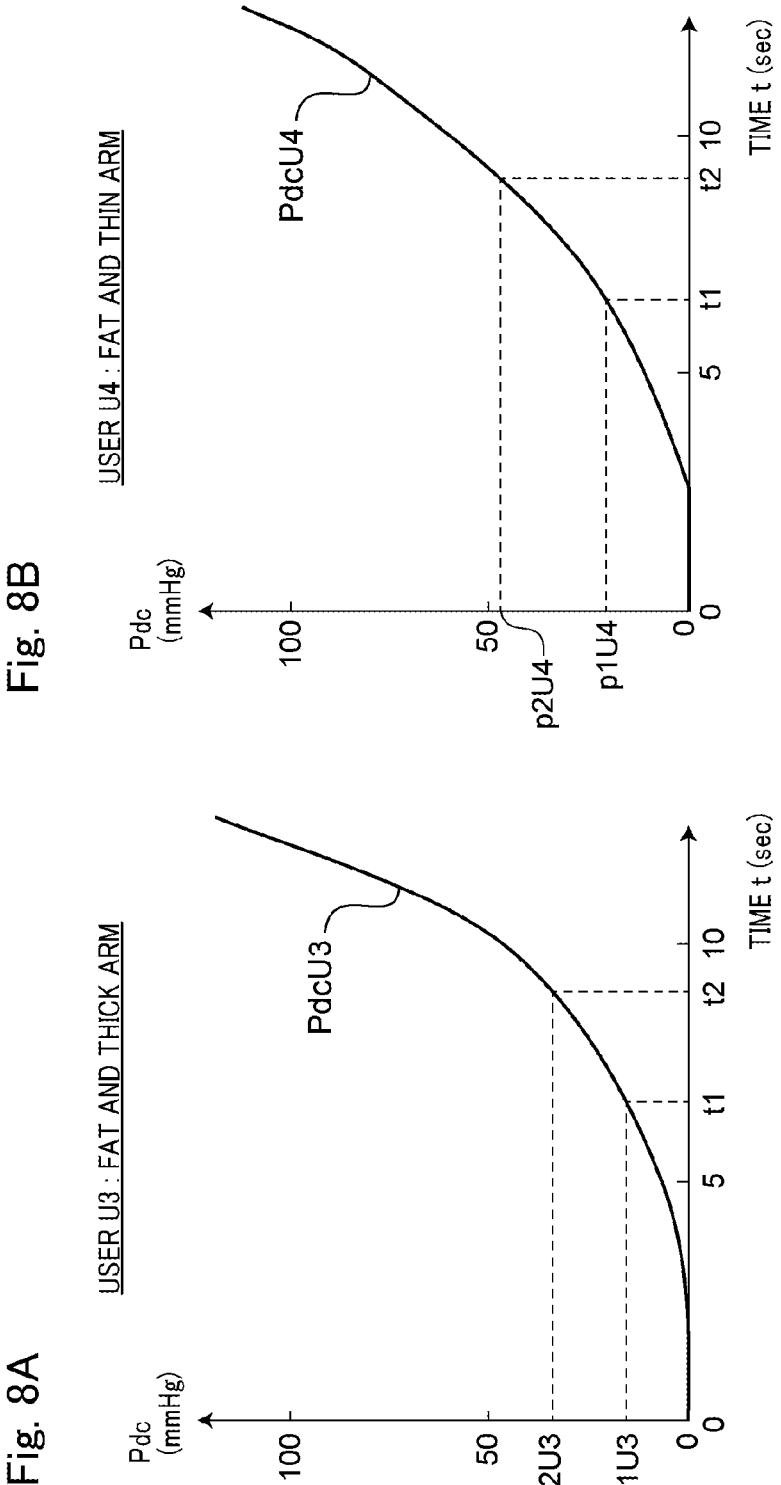

FIG. 8A is a diagram illustrating a direct-current pressure
change pattern with the lapse of time from the start of
pressurization for a fat and thick arm user.

FIG. 8B is a diagram illustrating a direct-current pressure
change pattern with the lapse of time from the start of
pressurization for a fat and thin arm user.

Figure 9:
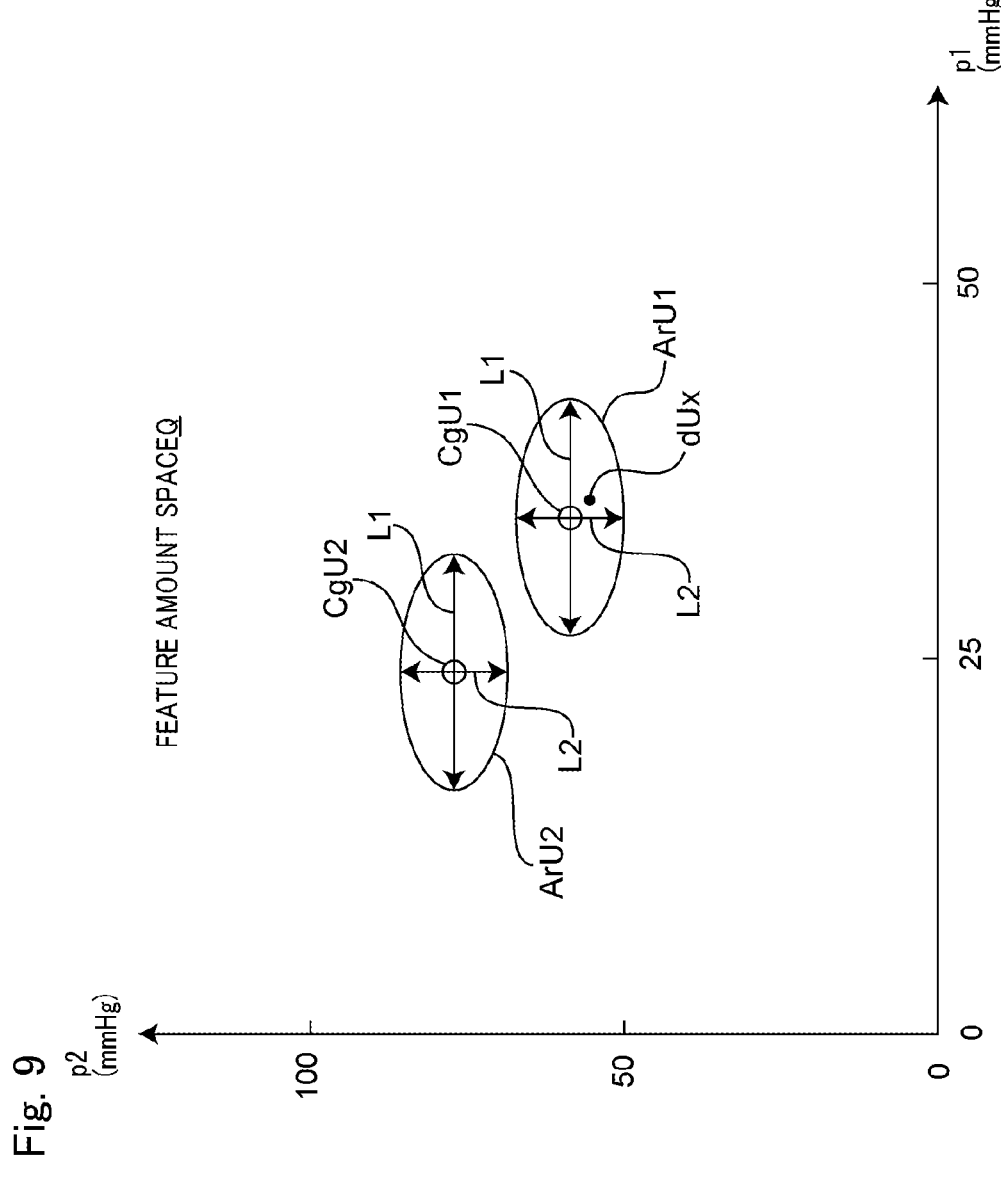

FIG. 9 is a diagram illustrating an allowable range (sub-
ject acceptance range) for determining whether or not a
subject to be authenticated is a registered user in a feature
amount space.

Figure 10:
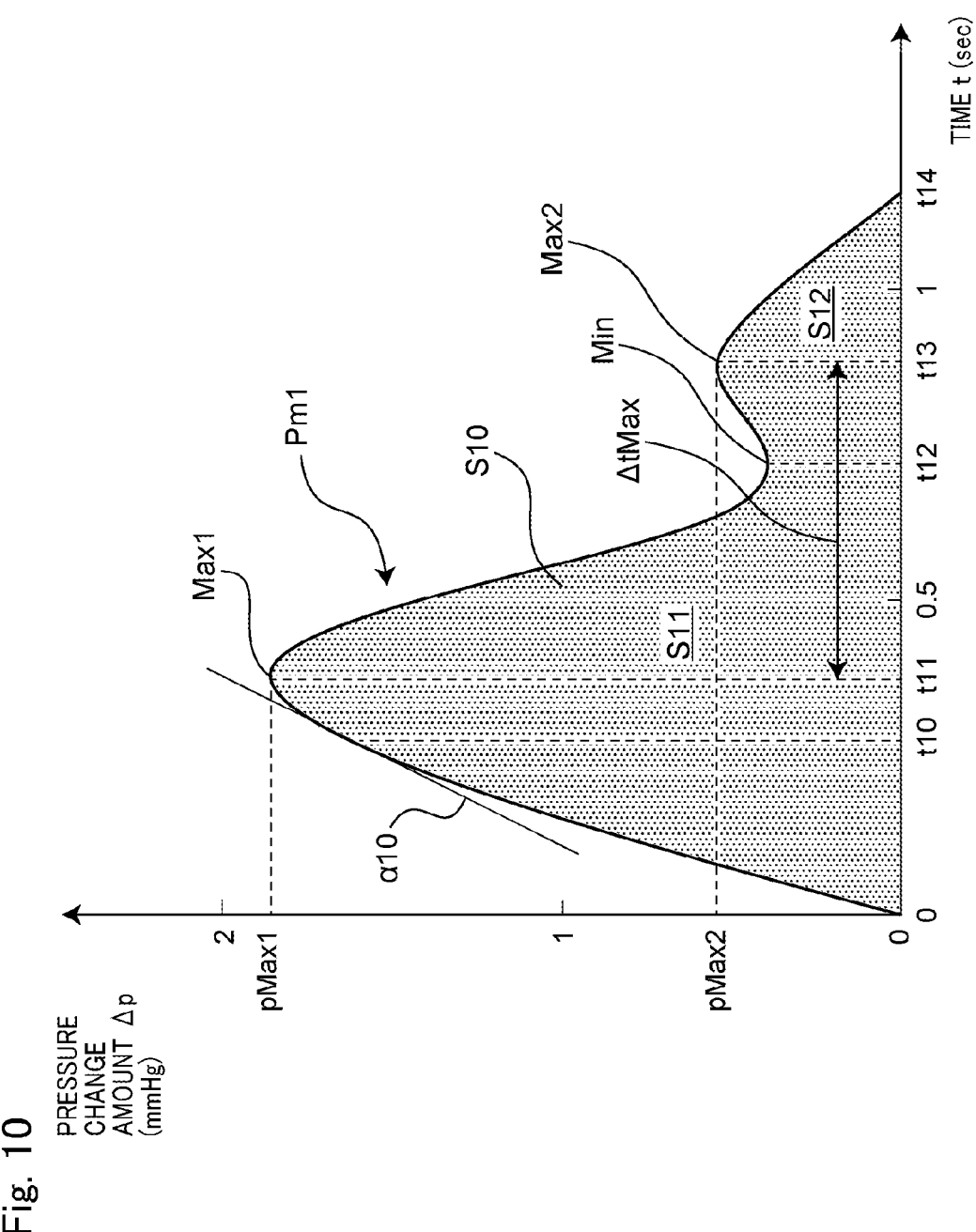

FIG. 10 is a diagram for explaining feature information
(one-beat feature amount) about a one-beat-by-beat wave-
form pattern.

Figure 11:
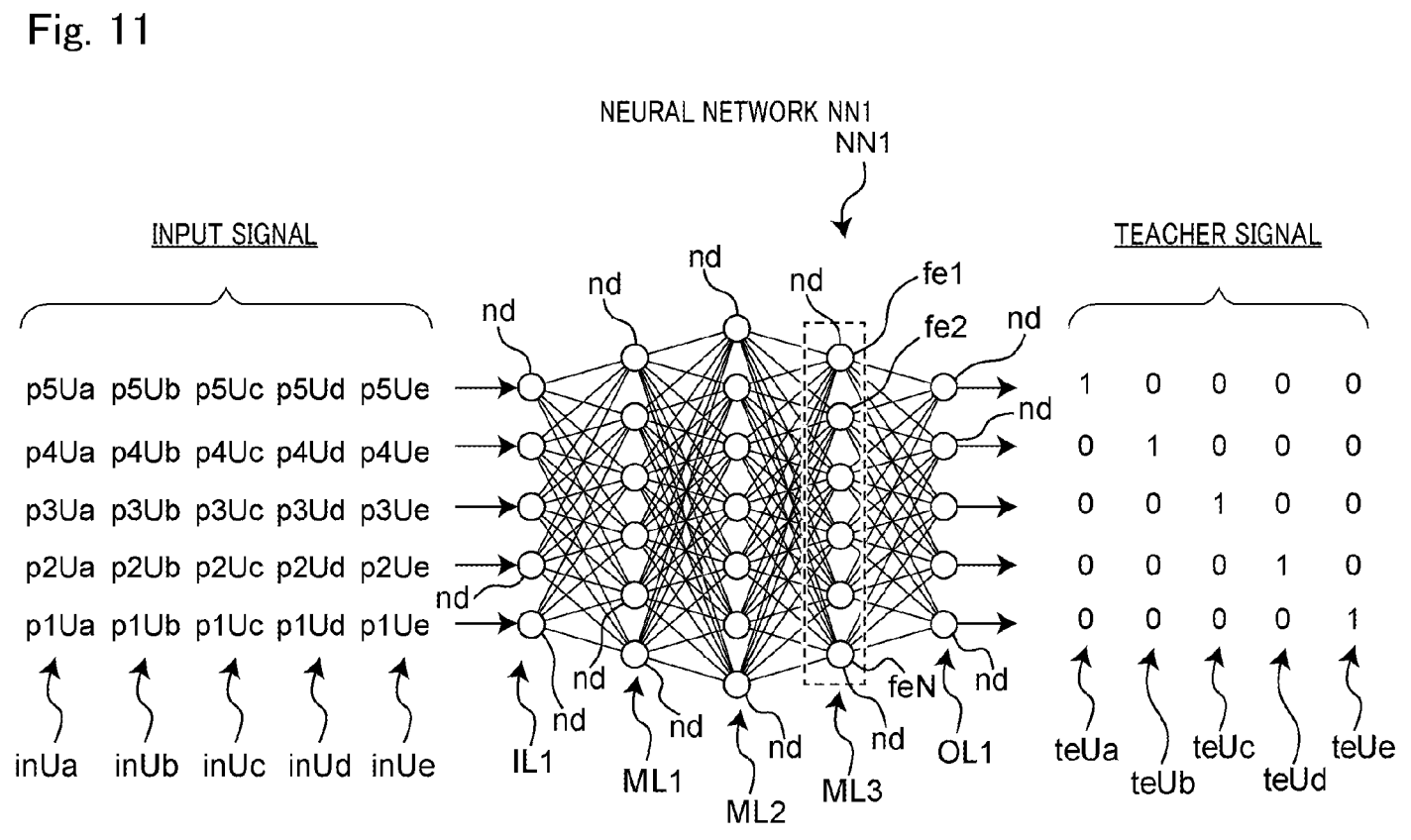

FIG. 11 is a diagram illustrating a configuration of a
neural network included in a sphygmomanometer according
to a modified example of the sphygmomanometer. FIG. 11
illustrates, in its left portion and right portion, an input signal
(feature vector) and a teacher signal provided to the neural
network in a learning stage, respectively.

Figure 12:
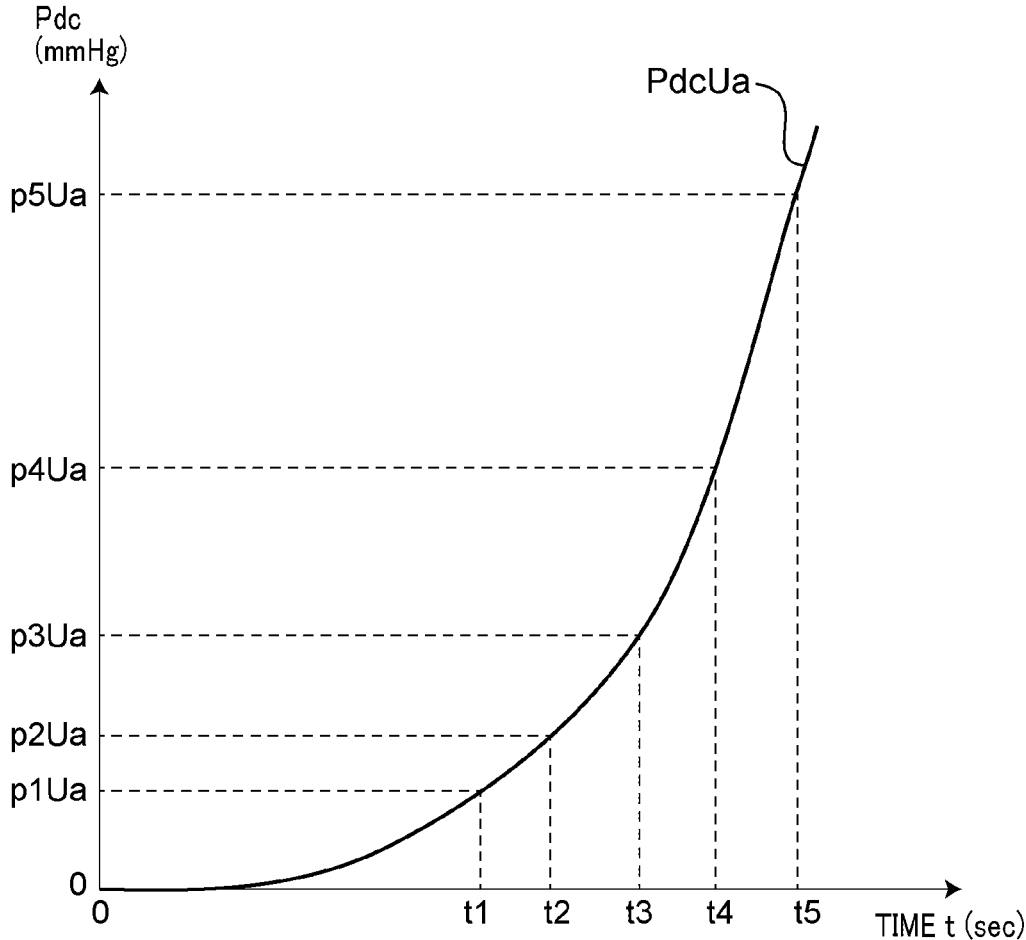

FIG. 12 is a diagram for explaining feature information
(feature vector) regarding a direct-current pressure change
pattern provided to the neural network.

DETAILED DESCRIPTION

Hereinafter, an embodiment of the present invention will
be described in detail with reference to the drawings.
(Configuration of Sphygmomanometer)

Figure 1:
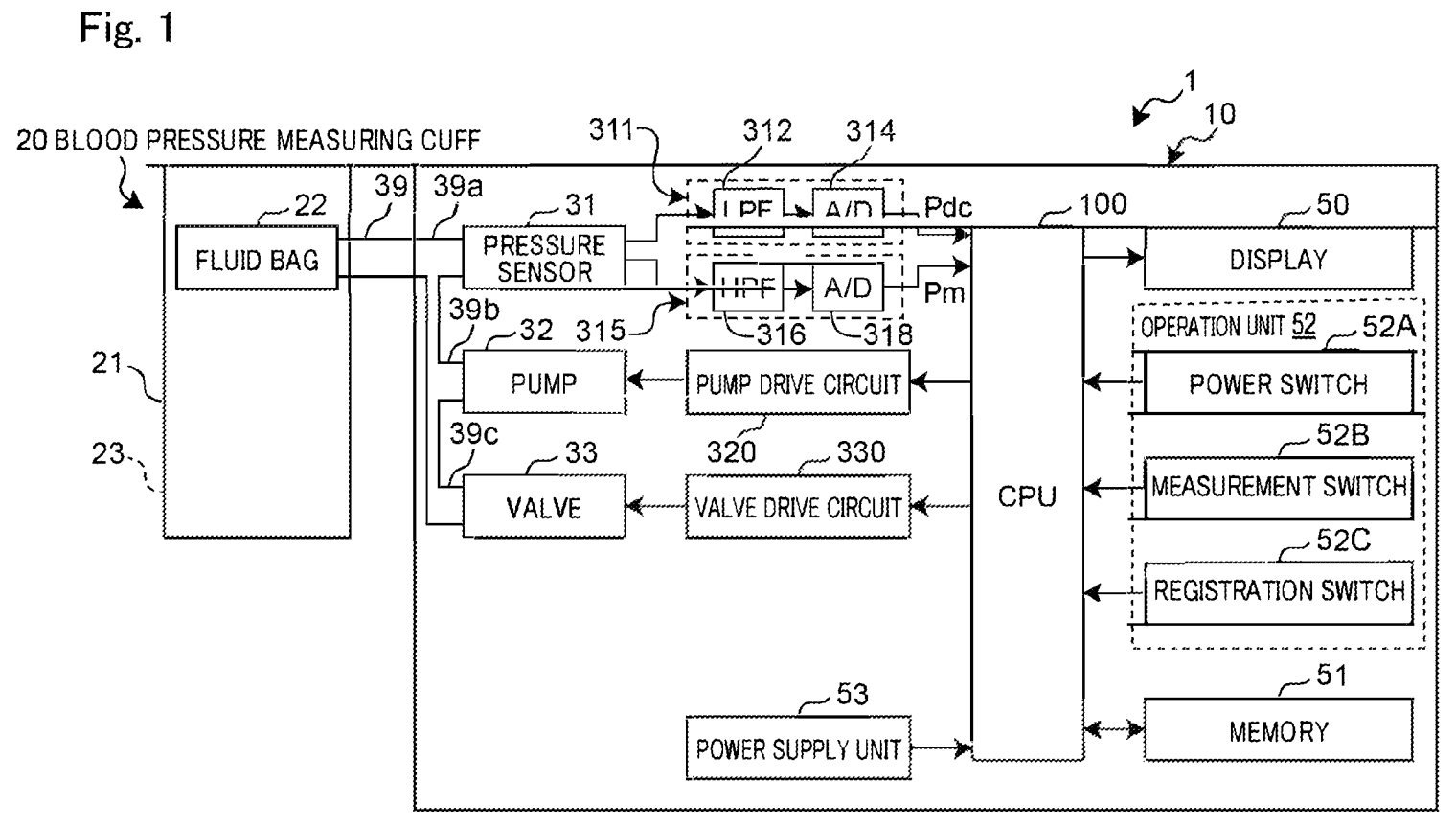

FIG. 1 illustrates an appearance of a sphygmomanometer
1 according to an embodiment of the present invention. The
sphygmomanometer 1 roughly includes a blood pressure
measuring cuff 20 worn around a rod-like site to be measured (for example, upper arm) of a subject, and a main body
10 on which elements for blood pressure measurement are
mounted.

The cuff 20 is a general cuff, and is configured by
sandwiching a fluid bag 22 between an elongated band-
shaped outer cloth 21 and an inner cloth 23, and sewing or
welding peripheral portions of the outer cloth 21 and the
inner cloth 23.

The main body 10 includes a central processing unit
(CPU) 100 as a processor, a display 50, an operation unit 52,
a memory 51 as a storage unit, a power supply unit 53, a
pressure sensor 31, a first filter unit 311 and a second filter
unit 315, a pump 32, a pump drive circuit 320, a valve 33,
and a valve drive circuit 330. In this example, an air pipe 39a
connected to the pressure sensor 31, an air pipe 39b con-
nected to the pump 32, and an air pipe 39c connected to the
valve 33 are joined to form one air pipe 39. The air pipe 39
is connected to the fluid bag 22 in the cuff 20 so as to be
capable of flowing a fluid. Hereinafter, the air pipes 39a, 39b
and 39c are collectively referred to as the air pipe 39.

In this example, the display 50 includes a liquid crystal
display (LCD), and displays predetermined information in
accordance with a control signal from the CPU 100. In this
example, the display 50 displays a systolic blood pressure
SBP (unit: mmHg), a diastolic blood pressure DBP (unit:
mmHg), a pulse rate (unit: beat/min) and a result of the
personal authentication for the subject. Note that the display
50 may be an organic electro luminescence (EL) display, or
may include a light emitting diode (LED).

In this example, the operation unit 52 includes a power
switch 52A for turning on or off the power of the sphyg-
momanometer 1, a measurement switch 52B for receiving
an instruction to start a blood pressure measurement mode,
and a registration switch 52C for receiving an instruction to
start a registration mode, and inputs an operation signal
corresponding to an instruction of a user to the CPU 100.
Specifically, when the power switch 52A is turned on, the
sphygmomanometer 1 enters a power-on state in which the
operation of the measurement switch 52B and the registra-
tion switch 52C by the user can be received. When the
measurement switch 52B is pressed in the power-on state,
the sphygmomanometer 1 executes processing in a mea-
surement mode (processing including blood pressure mea-
surement and personal authentication) to be described later.
When the registration switch 52C is pressed in the power-on
state, the sphygmomanometer 1 executes processing in a
registration mode (processing of performing registration
related to the user) to be described later. In the following
description, it is assumed that the sphygmomanometer 1 is
in the power-on state.

The memory 51 stores data of a program for controlling
the sphygmomanometer 1, setting data for setting various
functions of the sphygmomanometer 1, data of a measure-
ment result of the blood pressure value, registered feature
information serving as a reference for comparison for per-
sonal authentication, and the like. Furthermore, the memory
51 is used as a work memory or the like when the program
is executed.

Figure 2:
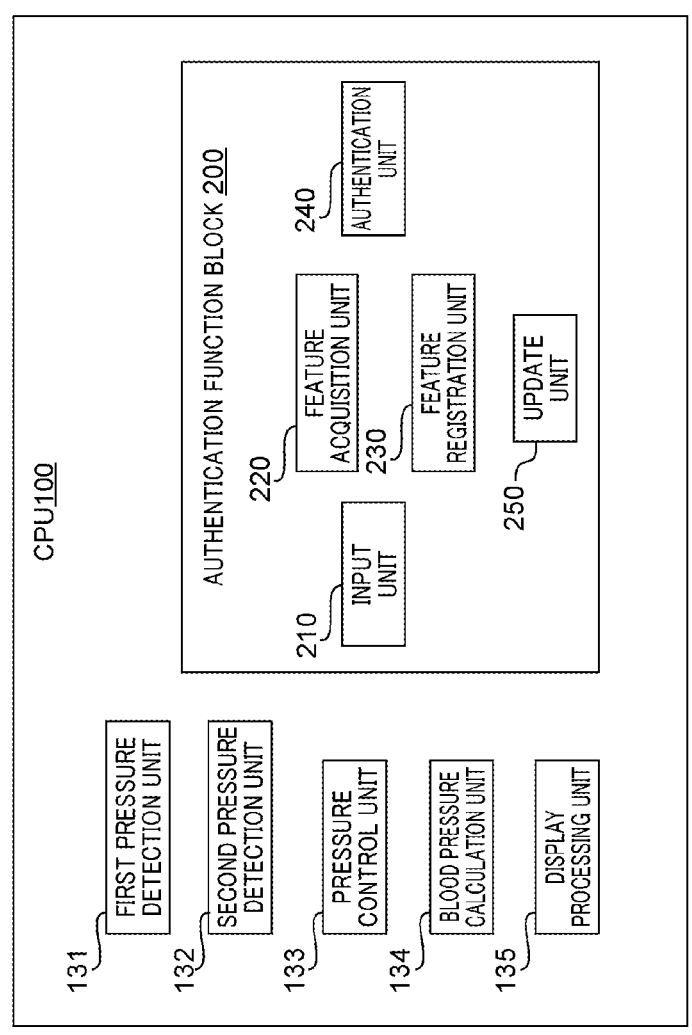
FIG. 2 is a diagram illustrating a functional block con-
figuration by a CPU of the sphygmomanometer.

The CPU 100 controls the operation of the entire sphyg-
momanometer 1 according to a program for controlling the
sphygmomanometer 1 stored in the memory 51. Specifically,
as illustrated in FIG. 2, the CPU 100 acts as a first pressure
detection unit 131, a second pressure detection unit 132, a
pressure control unit 133, a blood pressure calculation unit
134, and a display processing unit 135. Moreover, the CPU
100 acts as an input unit 210, a feature acquisition unit 220,
a feature registration unit 230, an authentication unit 240, and an update unit 250, which are included in the authentication function block 200. A specific function of each unit will be described later.

The pressure sensor 31 illustrated in FIG. 1 includes a piezoresistive semiconductor pressure sensor and an oscillation circuit in this example. The pressure sensor 31 is a piezoresistive pressure sensor in this example, and outputs the pressure (cuff pressure) Pc (see FIG. 6, lower section) in the fluid bag 22 contained in the cuff 20 as an electric resistance due to piezoresistive effect through the air pipe 39. The oscillation circuit oscillates at an oscillation frequency corresponding to the electric resistance from the semiconductor pressure sensor, and outputs a frequency signal including the oscillation frequency as a signal representing the cuff pressure Pc. The first filter unit 311 includes a low-pass filter (LPF) 312 and an A/D converter 314, extracts a direct-current component (This is referred to as a "direct-current component Pdc".) from a frequency signal representing the cuff pressure Pc, and converts the component into a digital value. The second filter unit 315 includes a high-pass filter (HPF) 316 and an A/D converter 318, extracts a pressure fluctuation component (pulse wave signal) Pm (see FIG. 6, upper section) due to a pulse wave indicated by the site to be measured from a frequency signal indicating the cuff pressure Pc, and converts the pressure fluctuation component into a digital value. The digitized direct-current component Pdc and pulse wave signal Pm are fed to the CPU 100. The CPU 100 acts as the first pressure detection unit 131 to detect a direct-current pressure change pattern (for example, the pressure change pattern PdcU1 illustrated in FIG. 7A) according to the fed direct-current component Pdc. Furthermore, the CPU 100 acts as the second pressure detection unit 132 to detect a one-beat-by-beat waveform pattern (for example, a one-beat-by-beat waveform pattern Pm1 illustrated in FIG. 6, upper section.) according to the fed pulse wave signal Pm. The pressure sensor 31, the first filter unit 311, the second filter unit 315, the first pressure detection unit 131, and the second pressure detection unit 132 constitute a pressure detection unit that detects the pressure of the cuff 20 as a whole.

The pump 32 illustrated in FIG. 1 is driven by the pump drive circuit 320 based on a control signal given from the CPU 100 (acting as the pressure control unit 133), and supplies air to the fluid bag 22 included in the cuff 20 through the air pipe 39. As a result, the pressure (cuff pressure Pc) of the fluid bag 22 is increased.

The valve 33 is a normally-open type electromagnetic valve, is driven by the valve drive circuit 330 based on a control signal given from the CPU 100 (acting as the pressure control unit 133), and is opened or closed to control the cuff pressure by discharging or enclosing the air in the fluid bag 22 through the air pipe 39.

The power supply unit 53 supplies power to the CPU 100, the display 50, the memory 51, the pressure sensor 31, the pump 32, the valve 33, and other units in the main body 10.

(Blood Pressure Measurement)

FIG. 3 illustrates a flow of blood pressure measurement respectively executed in processing of a registration mode (FIG. 4) to be described later and processing of a measurement mode (FIG. 5) to be described later.

When a user (subject) instructs a start of the measurement mode with the measurement switch 52B provided on the main body 10 in a wearing state in which the cuff 20 is worn around the site to be measured (step S11 in FIG. 3), the CPU 100 first performs initialization (step S12). Specifically, the CPU 100 initializes a memory area for processing, stops the pump 32, and performs 0 mmHg adjustment (The atmospheric pressure is set to 0 mmHg.) of the pressure sensor 31 in a state where the valve 33 is opened.

Subsequently, the CPU 100 acts as the pressure control unit 133 to close the valve 33 (step S13), to drive the pump 32, and to start pressurizing the cuff 20 (step S14). That is, the CPU 100 supplies a constant flow rate of air per unit time from the pump 32 to the fluid bag 22 contained in the cuff 20 through the air pipe 39. At the same time, the pressure sensor 31 detects the pressure (cuff pressure) Pc in the cuff 20 (fluid bag 22) through the air pipe 39. Here, as illustrated in FIG. 6, in the cuff pressure Pc detected by the pressure sensor 31, a pressure fluctuation component (pulse wave signal) Pm due to a pulse wave is superimposed in addition to a smoothly monotonically increasing component (direct-current component Pdc). According to the direct-current component Pdc fed through the first filter unit 311, the CPU 100 acts as the first pressure detection unit 131 to detect a direct-current pressure change pattern (for example, a pressure change pattern PdcU1 illustrated in FIG. 7A), which rises while increasing its increase rate with the lapse of time from the start of pressurization (that is, its inclination is gradually increased with being curved in a downward convex shape.) (step S15 in FIG. 3). At the same time, the CPU 100 controls the pressurization speed by the pump 32 based on an output of the first pressure detection unit 131. By this pressurization, the artery passing through the measurement site is compressed and ischemic.

Next, when the cuff pressure Pc reaches a predetermined value Pu (In this example, Pu=200 mmHg is set as illustrated in FIG. 7B so as to sufficiently exceed an assumed blood pressure value of the subject.) based on the output of the first pressure detection unit 131, the CPU 100 stops the pump 32 (step S16 in FIG. 3).

Subsequently, the CPU 100 acts as the pressure control unit 133 to gradually open the valve 33. As a result, the cuff pressure Pc is reduced at a substantially constant speed (step S17 in FIG. 3). In this decompression process, the CPU 100 acts as the second pressure detection unit 132 to detect the pulse wave signal Pm (including the one-beat-by-beat waveform pattern Pm1) fed through the second filter unit 315 (step S18 in FIG. 3). Then, the CPU 100 acts as the blood pressure calculation unit 134, and attempts to calculate the blood pressure value (systolic blood pressure (SBP) and diastolic blood pressure (DBP)) by, for example, a known oscillometric method based on the pulse wave signal Pm having been acquired at this time (step S19 in FIG. 3). Furthermore, in this example, the CPU 100 calculates the pulse rate (beats/min) on the basis of the pulse wave signal.

In a case where the blood pressure value and the pulse rate cannot be calculated yet due to lack of data (No in step S20 in FIG. 3), the CPU 100 repeats the processing of steps S17 to S20 until the blood pressure value and the pulse rate can be calculated.

When the blood pressure value and the pulse rate can be calculated in this manner (Yes in step S20), the CPU 100 acts as the pressure control unit 133 to perform control to open the valve 33 and rapidly exhaust the air in the cuff 20 (fluid bag 22) (step S21).

Thereafter, the CPU 100 performs control to store the blood pressure value and the pulse rate in the memory 51 (step S22).

In the above example, the blood pressure value and the pulse rate are calculated in the depressurization process of the cuff 20 (fluid bag 22), but the present invention is not limited thereto, and the blood pressure value and the pulse rate may be calculated in the pressurization process of the cuff 20 (fluid bag 22).

(Processing in Registration Mode)

Figure 4:
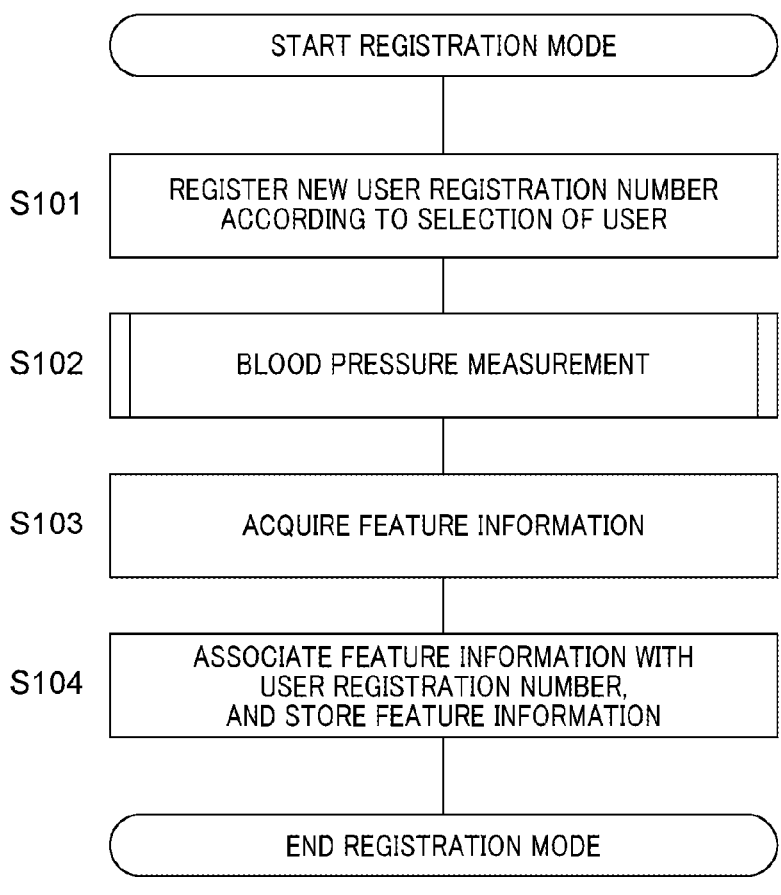
FIG. 4 is a diagram illustrating a flow of processing in a
registration mode by the sphygmomanometer.

FIG. 4 illustrates a flow of processing in the registration mode before personal authentication is performed by the sphygmomanometer 1. Here, it is assumed that a new user who has not yet registered the user registration number is, as a subject, in a wearing state in which the cuff 20 is worn around his/her upper arm as a site to be measured. In this state, when the user instructs a start of the registration mode using the registration switch 52C provided in the main body 10, the CPU 100 executes processing of the registration mode as follows.

First, in step S101 of FIG. 4, the CPU 100 causes the display 50 to display a screen for the user to select a new user registration number. For example, a candidate for the user registration number such as "Do you want to set new user registration number to U1?" is displayed on the display 50. At this time, when the user presses the registration switch 52C for a short time (within 1 second), for example, "U1" is registered in the memory 51 as the user registration number of the user. Instead, when the user presses the registration switch 52C for a long time (for 3 seconds or more), for example, the CPU 100 causes the display 50 to display another candidate for the user registration number such as "Do you want to set new user registration number to U2?". At this time, for example, when the user presses the registration switch 52C for a short time, "U2" is registered in the memory 51 as the user registration number of the user. In this manner, the CPU 100 causes the display 50 to sequentially display the candidates U1, U2, . . . of the user registration number, and registers the user registration number unique to the user in the memory 51 according to the selection of the user. Note that, in the following description, for the sake of simplicity, each user is represented by his/her user registration number.

Subsequently, in step S102 of FIG. 4, the CPU 100 executes the blood pressure measurement processing described with reference to FIG. 3. As described above, in step S15 of FIG. 3, the direct-current pressure change pattern is detected according to the direct-current component Pdc of the cuff pressure Pc in the pressurization process of the cuff 20. For example, FIGS. 7A to 8B illustrate various pressure change patterns, each of which rises while increasing its increase rate with the lapse of time from the start of pressurization (That is, its inclination is gradually increased with being curved in a downward convex shape.) on a time vs. cuff pressure (t-Pc) plane, where a horizontal axis represents the time t and a vertical axis represents the cuff pressure Pc. Specifically, FIG. 7A illustrates a typical pressure change pattern PdcU1 detected for a muscular and thick arm user U1. Furthermore, FIG. 7B illustrates a typical pressure change pattern PdcU2 detected for a muscular and thin arm user U2. FIG. 8A illustrates a typical pressure change pattern PdcU3 detected for a fat and thick arm user U3. FIG. 8B illustrates a typical pressure change pattern PdcU4 detected for a fat and thin arm user U4. Hereinafter, a reference sign PdcU is used to collectively refer to any of such direct-current pressure change patterns. Furthermore, in step S18 of FIG. 3, the pulse wave signal Pm (including the one-beat-by-beat waveform pattern Pm1) is detected as the pressure fluctuation component due to the pulse wave in the depressurization process of the cuff 20. In this example, the CPU 100 acts as the input unit 210 to feed the acquired direct-current pressure change pattern PdcU to the authentication function block 200. Note that, in addition to the direct-current pressure change pattern, the one-beat-by-beat waveform pattern Pm1 may be fed to the authentication function block 200 (This case will be described later.).

Hereinafter, it is assumed that a physical quantity (for example, Pdc) is followed by a reference sign (for example, U1) representing a user (or a subject) in order to represent that the physical quantity has been obtained for the user (or the subject).

Here, it is empirically known that the pressure change pattern (in particular, a direct-current pressure change pattern PdcU) is determined depending on physical characteristics of the subject such as a peripheral length of the site to be measured (thick arm or thin arm), body composition (muscular or fat), and the like. For example, in a case of the thick arm (that is, when the peripheral length of the site to be measured is large,) as illustrated in FIGS. 7A and 8A, the internal capacity of the cuff 20 (fluid bag 22) increases as compared with the case of the thin arm (that is, when the peripheral length is small,) as illustrated in FIGS. 7B and 8B. Therefore, when the fluid is supplied to the cuff 20 at a constant flow rate per unit time in the process of pressurizing the cuff 20, the increase rate (gradient) in the cuff pressure Pc tends to be small. Furthermore, as illustrated in FIGS. 8A and 8B, in a case where the site to be measured is fat, the site to be measured is more likely to be crushed in a high pressure range (for example, 25 mmHg or more) as compared with a case where the site to be measured is muscular as illustrated in FIGS. 7A and 7B, and thus the increase rate (gradient) in the cuff pressure tends to be small in the high pressure range. These tendencies appear in combination according to a combination of the peripheral length, the body composition, and the like of the site to be measured for each subject (user).

Subsequently, in step S103 in FIG. 4, the CPU 100 acts as the feature registration unit 230 to acquire feature information on the direct-current pressure change pattern PdcU in this example. Specifically, for example, for the user U1, values p1U1 and p2U1 taken by the pressure change pattern PdcU1 illustrated in FIG. 7A at predetermined times t1 and t2 (In this example, 0<t1<t2<10 seconds.) from the start of pressurization (Time t=0 second, cuff pressure Pc=0 mmHg) are acquired as direct-current feature amounts. Similarly, for the user U2, values p1 U2 and p2U2 taken by the pressure change pattern PdcU2 illustrated in FIG. 7B at times t1 and t2 are acquired as direct-current feature amounts. Furthermore, for the user U3, values p1 U3 and p2U3 taken by the pressure change pattern PdcU3 illustrated in FIG. 8A at times t1 and t2 are acquired as direct-current feature amounts. Furthermore, for the user U4, values p1U4 and p2U4 taken by the pressure change pattern PdcU4 illustrated in FIG. 8B at times t1 and t2 are acquired as direct-current feature amounts. Since the direct-current feature amounts (They are collectively denoted by reference signs p1 and p2.) for the pressure change pattern PdcU are determined depending on the physical characteristics of the subject (user) as described above, they can be suitably used as a determination criterion of the personal authentication.

Subsequently, in step S104 in FIG. 4, the CPU 100 further acts as the feature registration unit 230 to associate the feature information (in this example, the direct-current feature amounts p1 and p2) with the user registration number, and to store (registers) the feature information in the memory 51 as registered feature information. For example, when the direct-current feature amounts acquired for the user U1 are p1 U1 and p2U1, the direct-current feature amounts p1U1 and p2U1 are stored in the memory 51 as illustrated in a registration information table of Table 1 below. Furthermore, in a case where the direct-current feature amounts acquired for the user U2 different from the user U1 are p1U2 and p2U2, the direct-current feature amounts p1U2 and p2U2 are stored separately from those of the user U1. The same applies to still another user.

TABLE 1

| Registration information table | | |
|---|---|---|
| | Registered feature information | |
| User registration number | Direct-current feature amount p1 | Direct-current feature amount p2 |
| U1 | p1U1 | p2U1 |
| U2 | p1U2 | p2U2 |
| . . . | . . . | . . . |

In this way, by executing the processing of the registration mode in advance before performing the personal authentication, the registered feature information can be stored (registered) as a comparison criterion for the personal authentication of the user.

Moreover, in this example, in step S102 of FIG. 4, the blood pressure measurement process described with reference to FIG. 3 is repeated for a certain user, for example, three times or more in the resting state. In step S103 of FIG. 4, it is assumed that the direct-current pressure change pattern PdcU is detected every time the blood pressure is measured three or more times, and in step S104 of FIG. 4, feature information (in this example, the direct-current feature amounts p1 and p2) about the direct-current pressure change pattern PdcU is registered in the registration information table. Therefore, in this example, three or more values of data of the direct-current feature amounts p1U1 and p2U1 are registered for the user U1. Also for the user U2, three or more values of data of the direct-current feature amounts p1U2 and p2U2 are registered. The same applies to still another user.

(Processing in Measurement Mode)

Figure 5:
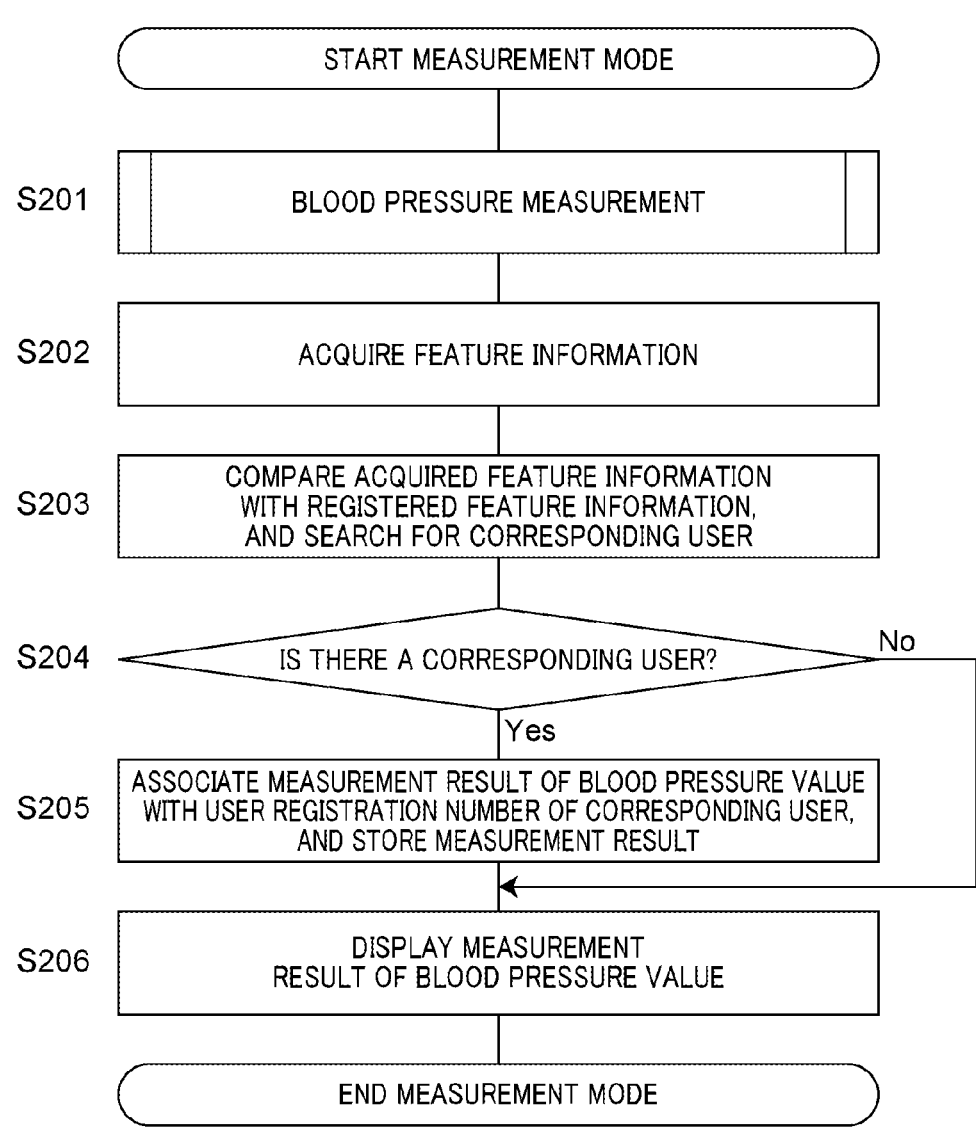
FIG. 5 is a diagram illustrating a flow of processing in a
measurement mode by the sphygmomanometer.

FIG. 5 illustrates a flow of processing in a measurement mode including blood pressure measurement and personal authentication by the sphygmomanometer 1. Here, it is assumed that a subject (This is represented by a reference sign Ux.) to be authenticated is in a wearing state in which the cuff 20 is worn around his/her upper arm as a site to be measured. In this state, when the subject Ux instructs a start of the measurement mode by the measurement switch 52B provided in the main body 10, the CPU 100 executes processing of the measurement mode as follows.

First, in step S201 of FIG. 5, the CPU 100 executes the blood pressure measurement process described with reference to FIG. 3. As described above, in step S15 of FIG. 3, for the subject Ux, the direct-current pressure change pattern (This is represented by a symbol PdcUx.) is detected as the direct-current component Pdc of the cuff pressure Pc by the pressurization process of the cuff 20. Furthermore, in step S18 of FIG. 3, for the subject Ux, the pulse wave signal Pm (including the one-beat-by-beat waveform pattern Pm1) is detected as the pressure fluctuation component due to the pulse wave in the depressurization process of the cuff 20. In this example, the CPU 100 acts as the input unit 210 to feed the direct-current pressure change pattern PdcUx to the authentication function block 200. In step S22 of FIG. 3, the CPU 100 stores the blood pressure value and the pulse rate in the memory 51.

Next, in step S202 of FIG. 5, the CPU 100 acts as the feature acquisition unit 220 to acquire feature information on the direct-current pressure change pattern PdcUx in this example. Specifically, for example, values (These are represented by reference signs p1Ux and p2Ux.) taken by the pressure change pattern PdcUx at predetermined times t1 and t2 (In this example, 0<t1<t2<10 seconds.) (see FIG. 7A) from the start of pressurization (time t=0 second, cuff pressure Pc=0 mmHg) are acquired as direct-current feature amounts.

Next, in step S203 of FIG. 5, the CPU 100 acts as the authentication unit 240 to compare the acquired feature information (in this example, the direct-current feature amounts p1Ux and p2Ux) with the registered feature information in the registration information table of Table 1, and thereby to search for a user corresponding to the subject Ux.

Specifically, as illustrated in FIG. 9, the CPU 100 creates a feature amount space Q in which the horizontal axis represents the direct-current feature amount p1 and the vertical axis represents the direct-current feature amount p2. In this example, the gravity center point CgU1 in the feature amount space Q is calculated using the data in which three or more values of the direct-current feature amounts p1U1 and p2U1 are registered for the user U1 in the registration information table of Table 1. Similarly, for the user U2, the gravity center point CgU2 in the feature amount space Q is calculated using the data in which three or more values of the direct-current feature amounts p1U2 and p2U2 are registered. For still another user, the gravity center point in the feature amount space Q is similarly calculated.

Moreover, the CPU 100 sets fixed ranges as subject acceptance ranges ArU1, ArU2, . . . , respectively, around the gravity center points CgU1, CgU2, . . . . Here, the "subject acceptance range" means an allowable range in which the subject Ux to be authenticated should be recognized as one of the users U1, U2, . . . registered in advance. In this example, each of the subject acceptance ranges ArU1, ArU2, . . . is set as an elliptical range in which the allowable width for the direct-current feature amount p1 is the major diameter L1 and the allowable width for the direct-current feature amount p2 is the minor diameter L2. The sizes of these subject acceptance ranges ArU1, ArU2, . . . are fixed values, and are adjusted such that both a person-in-question acceptance error (an error in which the person in question is recognized as another person) and a person-in-question rejection error (an error in which the person in question is recognized as not the person in question) become minimum values on the basis of experimental data obtained in advance for a large number of people.

Moreover, the CPU 100 determines whether or not a point (This is represented by a symbol dUx.) corresponding to the direct-current feature amounts p1Ux and p2Ux of the subject Ux falls within any one of the subject acceptance ranges ArU1, ArU2, . . . in the feature amount space Q. In this way, the CPU 100 searches for a user corresponding to the subject Ux. This search is performed while comparing the direct-current feature amounts p1Ux and p2Ux acquired for the subject Ux with the registered feature information (in this example, the direct-current feature amounts) of the users U1, U2, . . . .

Here, in a case where the point dUx corresponding to the direct-current feature amounts p1Ux and p2Ux of the subject Ux does not fall within any one of the subject acceptance ranges ArU1, ArU2, . . . (No in step S204 in FIG. 5), the CPU 100 determines that the subject Ux is not the user U1, U2, . . . registered in advance. In this case, the process proceeds to step S206 in FIG. 5, and the CPU 100 acts as the display processing unit 135 to simply display the measurement results of the blood pressure value and the pulse rate on the display 50.

On the other hand, when the point dUx corresponding to the direct-current feature amounts p1Ux and p2Ux of the subject Ux falls within any one of the subject acceptance ranges ArU1, ArU2, . . . (Yes in step S204 in FIG. 5), the subject Ux is determined to be a user registered in advance. In this case, in step S205 of FIG. 5, the CPU 100 stores the measurement result of the blood pressure value in the memory 51 in association with the user registration number of the user. In the example of FIG. 9, since the point dUx corresponding to the direct-current feature amounts p1Ux and p2Ux of the subject Ux is within the subject acceptance range ArU1 of the user U1, the CPU 100 stores the blood pressure value and the pulse rate obtained in step S201 of FIG. 5 in the memory 51 in association with the user registration number U1 of the user U1 as illustrated in a measurement result table of Table 2 below. In this example, it is assumed that the systolic blood pressure SBP is 130 (mmHg), the diastolic blood pressure DBP is 80 (mmHg), and the pulse rate is 70 (beats/min). Moreover, the process proceeds to step S206 in FIG. 5, and the CPU 100 acts as the display processing unit 135 to display the measurement results of the blood pressure value and the pulse rate on the display 50.

TABLE 2

Measurement result table

| User registration number | Systolic blood pressure SBP (mmHg) | Diastolic blood pressure DBP (mmHg) | Pulse rate (beats/ min) |
|---|---|---|---|
| U1 | 130 | 80 | 70 |
| U2 | . . . | . . . | . . . |
| . . . | . . . | . . . | . . . |

Note that the registration information table in Table 1 and the measurement result table in Table 2 may be associated with each other by a user registration number to form an integrated table.

As described above, in the sphygmomanometer 1, the personal authentication of the subject is performed using the feature information (In this example, the direct-current feature amounts p1 and p2) about the pressure change pattern, which rises while increasing its increase rate with the lapse of time from the start of pressurization in the pressurization process of the cuff 20. As described above, it is empirically known that this pressure change pattern (in particular, a direct-current pressure change pattern PdcU) is determined depending on the physical characteristics of the subject such as the peripheral length of the site to be measured (thick arm or thin arm), body composition (muscular or fat), and the like. These physical characteristics have an only small amount of change in a short period of time in an individual subject. In other words, these physical characteristics have an only small variation from measurement to measurement, unlike Korotkoff sounds and electrocardiographic signals. In the sphygmomanometer 1, since the personal authentication is performed using the feature information about the pressure change pattern determined depending on the physical characteristics of the subject, the personal authentication can be accurately performed on the subject. Furthermore, in a case where the personal authentication for the subject is performed in this manner, it is not necessary to provide an extra component (for example, a sound detecting device such as a microphone, an electrocardiographic electrode, and the like) that is not used for pressure observation.

Therefore, the sphygmomanometer 1 can be configured at low cost with a simple configuration.

Furthermore, in the sphygmomanometer 1, by appropriately setting the subject acceptance ranges ArU1, ArU2, . . . , it is possible to more accurately determine whether the subject Ux to be authenticated is the users U1, U2, . . . registered in advance.

In the above example, the subject acceptance ranges ArU1, ArU2, . . . are set as elliptical ranges, but the present invention is not limited thereto. For example, allowable ranges may be set independently for p1 on the horizontal axis and p2 on the vertical axis, and the subject acceptance range may be set as a rectangular range. In addition, the subject acceptance range can be set using a known method such as Euclidean distance, Manhattan distance, cosine similarity, Pearson's product-moment correlation coefficient, or dynamic time warping method.

Furthermore, in the above example, the values p1 and p2 taken by the direct-current pressure change pattern PdcU at the two predetermined times t1 and t2 from the start of pressurization are used as the direct-current feature amounts, but the present invention is not limited thereto. As the direct-current feature amounts, for example, values p1, p2, p3, . . . taken by the direct-current pressure change pattern PdcU at three or more predetermined times t1, t2, t3, . . . from the start of pressurization may be used. In addition, the following various feature amounts can be used as the direct-current feature amounts.

Time interval $\Delta t2'=-t1'$ (where t1' and t2' are times at which predetermined pressures p1 and p2' are reached, respectively.) from a predetermined pressure p1' to another pressure p2'

Pressure ratio (p2/p1)

Slope $\alpha$ between predetermined times t1 and t2, where $\alpha=(p2-p1)/(t2-t1)$ Gradient at predetermined time Areas S1 and S2 (Here, as exemplified in FIG. 7A, S1 is an area from time 0 to time t1 (indicated by stippling), and S2 is an area from time t1 to time t2 (indicated by hatching).)

Area ratio S2/S1

Modified Example 1

In the above example, only the direct-current feature amount of the direct-current pressure change pattern PdcU is used as the feature information, but the present invention is not limited thereto. As the feature information, in addition to the direct-current feature amount, a feature amount (i.e., one-beat feature amount) for the one-beat-by-beat waveform pattern Pm1 (see FIG. 6, upper section) may be used.

In this case, in step S102 of FIG. 4 (in particular, step S18 in FIG. 3) before the personal authentication is performed by the sphygmomanometer 1, the CPU 100 acts as the input unit 210 to feed the one-beat-by-beat waveform pattern Pm1 to the authentication function block 200 in addition to the direct-current pressure change pattern PdcU. Moreover, in step S103 of FIG. 4, the CPU 100 acts as the feature registration unit 230 to acquire, as the feature information, the one-beat feature amount for the one-beat-by-beat waveform pattern Pm1 in addition to the direct-current feature amount for the direct-current pressure change pattern PdcU.

Here, FIG. 10 illustrates an enlarged one-beat-by-beat waveform pattern Pm1. Specifically, FIG. 10 illustrates a typical one-beat-by-beat waveform pattern Pm1, where the start point of one beat is t=0 second and the pressure=0 mmHg, a horizontal axis is the elapsed time t from the start point, and a vertical axis is the pressure change amount $\Delta p$ from the start point. In this example, the one-beat-by-beat waveform pattern Pm1 rises from the start point with convexly curving upward, indicates the first maximum point (ejection peak) Max1 at time t11, indicates the minimum point Min at time t12, indicates the second maximum point (reflection peak) Max2 at time t13, and ends at a pressure of 0 mmHg (end point) at time t14. As such one-beat feature amounts for the one-beat-by-beat waveform pattern Pm1, the following various feature amounts exemplified in FIG. 10 can be used.

Pressure change amount (amplitude) pMax1 at first maximum point Max1, and pressure change amount (amplitude) pMax2 at second maximum point Max2

Time interval $\Delta t$Max between the first maximum point Max1 and the second maximum point Max2 ($=$t13$-$t11)

Gradient $\alpha 10$ after a lapse of a certain time t10 from the start point

Area S10 between one-beat-by-beat waveform pattern Pm1 and horizontal axis t

Ratio (pMax1/pMax2) between amplitude pMax1 at first maximum point Max1 and amplitude pMax2 at second maximum point Max2

Ratio (S11/S12) between an area S11 from time t=0 to time t12 and an area S12 from time t=t12 to time t14. in the area S10

Note that the one-beat-by-beat waveform pattern Pm1 can be extracted from either the pressurization process or the depressurization process illustrated in lower section of FIG. 6. However, as can be seen from upper section of FIG. 6, the waveform for each beat is most stable at the ending stage of the decompression process. Therefore, the one-beat-by-beat waveform pattern Pm1 is desirably extracted at the ending stage of the depressurization process.

Subsequently, in step S104 of FIG. 4, the CPU 100 further acts as the feature registration unit 230 to associate the one-beat feature amounts (for example, pMax1, pMax2) in addition to the direct-current feature amounts (for example, p1, p2) with the user registration number, and to store (register) the direct-current feature amount and the one-beat feature amounts in the memory 51 as registered feature information. For example, in a case where the user registration number of the user is U1, and the amplitude pMax1U1 at the first maximum point Max1 and the amplitude pMax2U1 at the second maximum point Max2 are acquired as one-beat feature amounts in addition to the direct-current feature amounts p1U1 and p2U1, the direct-current feature amounts p1U1, p2U1 and the one-beat feature amounts pMax1 U1, pMax2U1 are stored in the memory 51 as illustrated in a registration information table of Table 3 below.

TABLE 3

| Registration information table | | | | |
|---|---|---|---|---|
| | Registered feature information | | | |
| User registration number | Direct-current feature amount p1 | Direct-current feature amount p2 | One-beat feature amount pMax1 | One-beat feature amount pMax2 |
| U1 | p1U1 | p2U1 | pMax1U1 | pMax2U1 |
| U2 | p1U2 | p2U2 | . . . | . . . |
| . . . | . . . | . . . | . . . | . . . |

In this manner, before performing the personal authentication by the sphygmomanometer 1, in addition to the direct-current feature amount, the one-beat feature amount can be registered in the memory 51 as the registered feature information.

Thereafter, in step S201 of FIG. 5 (in particular, step S18 in FIG. 3) at the stage of performing the personal authentication by the sphygmomanometer 1, the CPU 100 acts as the input unit 210 to feed a one-beat-by-beat waveform pattern (This is represented by a symbol Pm1Ux.) to the authentication function block 200 in addition to the direct-current pressure change pattern PdcUx for the subject Ux. Subsequently, in step S202 of FIG. 5, the CPU 100 acts as the feature acquisition unit 220 to acquire followings as the feature information in this example.

The direct-current feature amounts p1Ux and p2Ux for the direct-current pressure change pattern PdcUx, and An amplitude pMax1 (This is represented by the symbol pMax1Ux.) at the first maximum point Max1 and an amplitude pMax2 (This is represented by the symbol pMax2Ux.) at the second maximum point Max2, as one-beat feature amounts for the one-beat-by-beat waveform pattern Pm1Ux.

Next, in step S203 of FIG. 5, the CPU 100 acts as the authentication unit 240 to compare the acquired feature information (In this example, the direct-current feature amounts p1Ux, p2Ux and the one-beat feature amounts pMax1Ux, pMax2Ux) with the registered feature information in the registration information table of Table 2, and to search for a user corresponding to the subject Ux. For example, the CPU 100 creates a four-dimensional feature amount space (This is represented by a symbol Q1.) having p1, p2, pMax1 and pMax2 as coordinate axes. In the feature amount space Q1, points corresponding to the registered feature information are calculated for the users U1, U2, . . . registered in advance. Also, allowable ranges (subject acceptance ranges), in each of which the subject Ux is to be recognized as a user registered in advance, are set respectively around the points corresponding to the registered feature information. Then, when the point corresponding to the feature information acquired for the subject Ux falls within the allowable range in the feature amount space Q1, the CPU 100 determines that the subject Ux is the user registered in advance (for example, U1), and when the point corresponding to the feature information acquired for the subject Ux does not fall within the allowable range, the CPU determines that the subject Ux is not the users U1, U2, . . . registered in advance. In this way, by using the one-beat feature amounts as a determination material in addition to the direct-current feature amounts, the personal authentication can be performed on the subject with higher accuracy.

Note that, under the predetermined first condition, it is desirable to use only the direct-current feature amount without using the one-beat feature amount for the personal authentication of the subject. Here, the "predetermined first condition" includes, for example, following conditions in which reliability of the one-beat feature amount is low.

A pulse rate when performing the personal authentication is significantly higher or lower than a pulse rate when the registered feature information was registered.

A blood pressure value when performing the personal authentication is significantly higher or lower than a blood pressure value when the registered feature information was registered.

The temperature, humidity, and atmospheric pressure when performing the personal authentication are significantly higher or lower than the temperature, humidity, and atmospheric pressure when the registered feature information was registered (In this case, the sphygmomanometer 1 observes and records the temperature, humidity, and atmospheric pressure every time the blood pressure is measured.).

Under such conditions in which reliability of the one-beat feature amount is low, it is possible to prevent the accuracy of the personal authentication from deteriorating by using only the direct-current feature amount without using the one-beat feature amount for the personal authentication for the subject.

Modified Example 2

In the above example, for the personal authentication on the subject, the CPU 100 creates the feature amount space Q (or Q1) and searches for the user corresponding to the subject Ux in the feature amount space Q, but the present invention is not limited thereto. For example, the sphygmomanometer 1 may include a learned neural network NN1 as illustrated in FIG. 11. and the user corresponding to the subject Ux may be determined using the neural network NN1.

Specifically, as illustrated in FIG. 11, the neural network NN1 includes an input layer ILL three intermediate layers ML1, ML2 and ML3, and an output layer OL1. In this example, each of the input layer IL1 and the output layer OL1 includes five nodes (neurons) nd. Each of the intermediate layers ML1, ML2 and ML3 includes 20 to 30 nodes nd.

In this example, coupling strengths between each of the nodes nd, nd have been weighted in the learning stage. Thereby, when any one of the feature informations inUa, inUb, inUc, inUd, inUe about the direct-current pressure change patterns PdcU of five teacher users (These are represented by symbols Ua, Ub, Uc, Ud, Ue.) is fed to the input layer IL1 as an input signal, the neural network NN1 generates, to the output layer OL1 via the intermediate layers ML1, ML2 and ML3, output information teUa, teUb, teUc, teUd or teUe representing a teacher user Ua, Ub, Uc, Ud or Ue corresponding to the fed feature information. That is, the neural network NN1 has been learned.

Specifically, as illustrated in FIG. 12, the feature information inUa regarding the pressure change pattern of the teacher user (For example, Ua) is determined in advance as values p1Ua, p2Ua, p3Ua, p4Ua, p5Ua taken by the pressure change pattern PdcUa at predetermined times t1, t2, t3, t4, t5 (In this example, $0 < t1 < t2 < t3 < t4 < t5$.), respectively, from the pressurization start (Time $t = 0$ second, and cuff pressure $Pc = 0$ mmHg) in the direct-current pressure change pattern (This is represented by a symbol PdcUa.) obtained in step S102 (in particular, step S18 in FIG. 3) in FIG. 4. A vector having these five values (p1Ua, p2Ua, p3Ua, p4Ua, p5Ua) as components is referred to as a feature vector inUa using the same code as that of the feature information inUa. Similarly, as illustrated in left portion of FIG. 11, the feature information inUb about the direct-current pressure change pattern PdcUb of the teacher user Ub is expressed by a feature vector inUb=(p1Ub, p2Ub, p3Ub, p4Ub, p5Ub). The feature information inUc about the direct-current pressure change pattern PdcUc of the teacher user Uc is expressed by a feature vector inUe=(p1Uc, p2Uc, p3Uc, p4Uc, p5Uc). The feature information inUd about the direct-current pressure change pattern PdcUd of the teacher user Ud is expressed by a feature vector inUd=(p1Ud, p2Ud, p3Ud, p4Ud, p5Ud). Furthermore, the feature information inUe regarding the direct-current pressure change pattern PdcUe of the teacher user Ue is expressed by a feature vector inUe=(p1Ue, p2Ue, p3Ue, p4Ue, p5Ue). In the learning stage, these feature vectors inUa, inUb, inUc, inUd and inUe are fed to the input layer IL1.

On the other hand, the output information teUa representing the teacher user (for example, Ua) is represented by an output vector teUa=(1, 0, 0, 0, 0) as illustrated in right portion of FIG. 11. Similarly, the output information teUb representing the teacher user Ub is represented by an output vector teUb=(0,1,0,0,0). The output information teUc representing the teacher user Uc is represented by an output vector teUc=(0,0,1,0,0). The output information teUd representing the teacher user Ud is represented by an output vector teUd=(0,0,0,1,0). The output information teUe representing the teacher user Ue is represented by an output vector teUe=(0,0,0,0,1). In the learning stage, for example, when the feature vector inUa for the teacher user Ua is fed to the input layer IL1, an output vector teUa representing the teacher user Ua is provided to the output layer OL1 as a teacher signal correspondingly. Similarly, when the feature vector inUa for the teacher user Ua is fed to the input layer IL1, an output vector teUa representing the teacher user Ua is correspondingly provided to the output layer OL1 as a teacher signal. Similarly, when the feature vector inUb for the teacher user Ub is fed to the input layer ILL an output vector teUb representing the teacher user Ub is correspondingly provided to the output layer OL1 as a teacher signal. Similar processing is performed for the other teacher users Uc, Ud and Ue.

By repeating such learning, each of the coupling strengths between the nodes nd, nd has been weighted, such that, when any one of the feature informations inUa, inUb, inUc, inUd, inUe about the direct-current pressure change pattern PdcU of the five teacher users Ua, Ub, . . . , Ue is fed to the input layer IL1 as an input signal, the neural network NN1 generates, to the output layer OL1 via the intermediate layers ML1, ML2 and ML3, the output information teUa, teUb, teUc, teUd or teUe representing the teacher users Ua, Ub, Uc, Ud or Ue corresponding to the fed feature information.

By providing such a neural network NN1, it is possible to perform personal authentication for the five teacher users Ua, Ub, . . . , Ue and/or a user group including users other than the teacher users. Next, processing in the registration mode and processing in the measurement mode in a case where the neural network NN1 is used will be described. (Processing of Registration Mode in Case of Using Neural Network)

In this case, the CPU 100 acts as the feature registration unit 230 to perform the following control in advance before performing the personal authentication. First, in the pressurization process of the cuff 20, for each user for a user group including the five teacher users Ua, Ub, . . . , Ue and/or users other than the teacher users, a feature vector inUy=(p1Uy, p2Uy, p3Uy, p4Uy, p5Uy) is acquired as feature information regarding the direct-current pressure change pattern PdcU of the user (This is represented by a reference sign Uy.). Next, for each user, the feature vector inUy acquired for the user Uy is fed to the input layer IL1 of the neural network NN1 to obtain information fe1Uy, fe2Uy, . . . , feNUy appearing in a certain intermediate layer (In this example, the intermediate layer ML3 immediately before the output layer OL1 is used.) among the plurality of intermediate layers ML1, ML2 and ML3. A vector having N (N=20 to 30) values as components is referred to as a feature artificial intelligence (AI) vector feUy for the user Uy. Note that, illustrated in FIG. 11 are components (fe1, fe2, . . . , feN) of a general feature AI vector fe in which the user is not limited. The individual components fe1, fe2, . . . , feN are referred to as AI feature amounts. Since it is known that the feature AI vector fe=(fe1, fe2, . . . , feN) can be used as the feature information for specifying the user, a detailed description thereof will be omitted. The CPU 100 stores (registers) the components of the feature AI vector feUy for the user Uy in the memory 51 as registered feature information in association with the user Uy as illustrated in the registration information table of Table 4 below. Similarly, when the user registration number of the user different from the user Uy is Uz and the acquired feature AI vector is inUz=(fe1Uz, fe2Uz, . . . , feNUz), the registered feature information of the user Uz is stored separately from the registered feature information of the user Uy. The same applies to still another user. As a result, as illustrated in the following registration information table of Table 4, for each of the users Uy, Uz, . . . , the registered feature information is stored in the memory 51.

TABLE 4

| Registration information table | | | | |
| --- | --- | --- | --- | --- |
| | Registered feature information | | | |
| User registration number | AI feature amount fe1 | AI feature amount fe2 | AI feature amount . . . | AI feature amount feN |
| Uy | fe1Uy | fe2Uy | . . . | feNUy |
| Uz | fe1Uz | fe2Uz | . . . | feNUz |
| . . . | . . . | . . . | . . . | . . . |

(Processing of Measurement Mode in Case of Using Neural Network)

At the stage of performing the personal authentication, the CPU 100 acts as the feature acquisition unit 220 to acquire feature information (In this example, the feature vector inUx=(p1Ux, p2Ux, p3Ux, p4Ux, p5Ux)) on the pressure change pattern PdcU of the subject (This is referred to as Ux.) to be authenticated by the pressurization process of the cuff 20.

Moreover, the CPU 100 acts as the authentication unit 240 to feed the feature AI vector inUx acquired for the subject Ux to the input layer IL1 of the neural network NN1, and to acquire the information appearing in the intermediate layer ML3 as a feature AI vector inUx=(fe1Ux, fe2Ux, . . . , feNUx)). Then, the CPU 100 compares the feature AI vector inUx=(fe1Ux, fe2Ux, . . . , feNUx) acquired for the subject Ux with the registered feature information of each of the users Uy, Uz, . . . registered in the registration information table of Table 4, and determines whether or not the subject Ux is a user included in the user group. As a result, in a case where the subject Ux is a user included in the user group, this can be authenticated.

Modified Example 3

Under a predetermined second condition, it is desirable to update the registered feature information registered in the registration information tables of Tables 1, 3 and 4 of the memory 51. Here, the "predetermined second condition" include, for example, the following conditions in which the registered feature information should be updated:

A certain period (For example, a period in which the feature information about the pressure change pattern may significantly change, such as six months.) has elapsed since a registration of the registered feature information (or a previous update).

The subject Ux is determined to be a pre-registered user (for example, U1), but the point dUx (see FIG. 9) corresponding to the feature information acquired for the subject Ux is far from the gravity center point CgU1 within the subject acceptance range ArU1.

Therefore, in the sphygmomanometer 1, the CPU 100 acts as the update unit 250 to update the registered feature information of the user under the predetermined second condition using the feature information acquired for the subject Ux when it is determined that the subject Ux is the user registered in advance. As a result, when the registered feature information should be updated, the registered feature information can be automatically updated and maintained in an appropriate state. As a result, it is possible to prevent the accuracy of the personal authentication from deteriorating.

Modified Example 4

Under a predetermined third condition, it is desirable to cancel the personal authentication. Here, the "predetermined third condition" include a condition in which reliability of the feature information (direct-current feature amount and/ or one-beat feature amount) about the pressure change pattern is regarded as low, for example, as follows:

Irregular pulse wave is detected (In this case, the sphygmomanometer 1 detects the irregular pulse wave based on the pulse rate.).

It is determined that body motion is occurring (In this case, the sphygmomanometer 1 includes an acceleration sensor to detect the body motion.).

Loose winding (i.e., a condition in which the cuff 20 is loosely wound around the site to be measured) is detected (In this case, the sphygmomanometer 1 detects the loose winding based on the fact that the pressure change pattern rises extremely calm.).

Therefore, in the sphygmomanometer 1, the CPU 100 acts as the authentication unit 240 to stop the personal authentication under the predetermined third condition. Accordingly, in a case where reliability of the feature information (the direct-current feature amount and/or the one-beat feature amount) about such a pressure change pattern is low, the personal authentication can be canceled. As a result, it is possible to prevent the accuracy of the personal authentication from deteriorating.

Furthermore, in the above embodiment, the site to be measured is the upper arm, but the present invention is not limited thereto. The site to be measured may be an upper limb other than the upper arm such as a wrist or a lower limb such as an ankle.

The above-described personal authentication method on a sphygmomanometer may be recorded as software (a computer program) on a non-transitory recording medium capable of storing data, such as a compact disc (CD), a digital universal disc (DVD), or a flash memory. By installing software recorded on such a recording medium in a substantial computer device such as a personal computer, a personal digital assistant (PDA), or a smartphone, the computer device can be caused to execute the above-described personal authentication method on a sphygmomanometer.

As described above, a sphygmomanometer of the present disclosure is a sphygmomanometer including a cuff configured to compress a site to be measured of a subject and measuring a blood pressure by observing a pressure of the cuff, the sphygmomanometer comprising:

a pressure control unit that performs control to supply a fluid to the cuff to pressurize the cuff or discharge the fluid from the cuff to depressurize the cuff;

a pressure detection unit that detects a pressure of the cuff;

a blood pressure calculation unit that calculates a blood pressure based on an output of the pressure detection unit;

a feature acquisition unit that acquires, for a subject to be authenticated, feature information on a pressure change pattern of the cuff with a lapse of time from a start of pressurization in a pressurization process of the cuff; and an authentication unit that compares the acquired feature information with registered feature information on a user registered in advance, and performs personal authentication on the subject.

In the present specification, the "pressure of the cuff" means a pressure in the cuff (typically, a fluid bag contained in the cuff). Hereinafter, the "pressure of the cuff" is appropriately abbreviated as a "cuff pressure".

The "pressure change pattern" means a pattern in which the pressure of the cuff changes with the lapse of time from the start of pressurization in the pressurization process of the cuff. A pressure fluctuation component due to a pulse wave indicated by the site to be measured is superimposed on the pressure of the cuff in addition to a smoothly monotonically increasing component (direct-current component).

To "perform personal authentication" means to determine whether or not the subject to be authenticated is a user (the person himself/herself) registered in advance. In the present specification, it is determined whether or not the subject is a user registered in advance according to whether or not the feature information regarding the pressure change pattern of the subject matches the registered feature information regarding the user registered in advance. Note that the "user registered in advance" may be singular or plural.

The "registered feature information" is typically feature information acquired by the feature acquisition unit and stored in a storage unit in advance before the personal authentication is performed.

In the sphygmomanometer of the present disclosure, blood pressure measurement is performed as follows. In a state where the cuff is worn on the site to be measured, the pressure control unit supplies a fluid to the cuff to pressurize the cuff or discharges the fluid from the cuff to depressurize the cuff. In the pressurization process by the pressurization or the subsequent depressurization process, the pressure detection unit detects a pressure of the cuff. The blood pressure calculation unit calculates a blood pressure based on an output of the pressure detection unit. In this manner, the blood pressure measurement is performed.

Furthermore, the personal authentication of the subject is performed as follows. The feature acquisition unit acquires, for the subject to be authenticated, feature information on a pressure change pattern, which rises while increasing its increase rate with the lapse of time from the start of the pressurization in the pressurization process of the cuff. The authentication unit compares the acquired feature information with registered feature information of a user registered in advance, and performs the personal authentication on the subject. Here, it is empirically known that the pressure change pattern (in particular, a direct-current pressure change pattern whose increase rate increases over time according to a direct-current component of the pressure of the cuff) is determined depending on physical characteristics of the subject such as a peripheral length of the site to be measured (thick arm or thin arm), a body composition (muscular or fat), and the like. For example, in a case where a peripheral length of the site to be measured is large (that is, in a case of a thick arm), an internal capacity of the cuff (fluid bag) increases as compared with a case where the peripheral length is small (that is, in a case of a thin arm). Therefore, when the fluid is supplied to the cuff at a constant flow rate per unit time in the process of pressurizing the cuff, the increase rate (gradient) in the cuff pressure tends to be small. Furthermore, in a case where the site to be measured is fat, the site to be measured is more likely to be crushed in a high pressure range as compared with a case where the site to be measured is muscular, and thus the increase rate (gradient) in the cuff pressure tends to be small in the high pressure range. These tendencies appear in combination according to a combination of the peripheral length, the body composition, and the like of the site to be measured for each subject. These physical characteristics have an only small amount of change in a short period of time in an individual subject. In other words, these physical characteristics have an only small variation from measurement to measurement, unlike Korotkoff sounds and electrocardiographic signals. In this sphygmomanometer, since the personal authentication is performed using the feature information about the pressure change pattern determined depending on the physical characteristics of the subject, the personal authentication can be accurately performed on the subject. Furthermore, in a case where the personal authentication for the subject is performed in this manner, it is not necessary to provide an extra component (for example, a sound detecting device such as a microphone, an electrocardiographic electrode, and the like) that is not used for pressure observation. Therefore, this sphygmomanometer can be configured at low cost with a simple configuration.

In the sphygmomanometer according to one embodiment, the authentication unit creates a feature amount space having, as coordinate axes, different feature amounts included in the feature information regarding the pressure change pattern, in the feature amount space, calculates a point corresponding to the registered feature information for the user registered in advance, and sets an allowable range in which the subject is recognized to be the user registered in advance around the point corresponding to the registered feature information; and in the feature amount space, determines that the subject is the user registered in advance when a point corresponding to the acquired feature information of the subject falls within the allowable range, and determines that the subject is not the user registered in advance when the point corresponding to the acquired feature information of the subject does not fall within the allowable range.

In the sphygmomanometer according to this one embodiment, whether or not the subject (subject to be authenticated) is the user registered in advance can be more accurately determined by appropriately setting the allowable range.

The sphygmomanometer according to one embodiment further comprises:

a first pressure detection unit that extracts, in the pressurization process of the cuff, a direct-current component from the pressure of the cuff, and thereby detects a direct-current pressure change pattern; and a second pressure detection unit that extracts, in the pressurization process of the cuff or a depressurization process subsequent to the pressurization process, a pressure fluctuation component due to a pulse wave indicated by the site to be measured from the pressure of the cuff, and thereby detects a one-beat-by-beat waveform pattern,

wherein the feature acquisition unit acquires, as the feature information, a one-beat feature amount of the one-beat-by-beat waveform pattern in addition to a direct-current feature amount of the direct-current pressure change pattern, and the authentication unit performs personal authentication on the subject by comparing the acquired one-beat feature amount with a one-beat feature amount registered in advance, in addition to comparing the acquired direct-current feature amount with a direct-current feature amount registered in advance.

The "direct-current feature amount" means a feature amount for a direct-current pressure change pattern. Furthermore, the "one-beat feature amount" means a feature amount for a one-beat-by-beat waveform pattern instead of the direct-current pressure change pattern.

In the sphygmomanometer according to this one embodiment, the first pressure detection unit extracts, in the pressurization process of the cuff, a direct-current component from the pressure of the cuff, and thereby detects a direct-current pressure change pattern in the pressurization process of the cuff. On the other hand, the second pressure detection unit extracts, in the pressurization process of the cuff or the depressurization process subsequent to the pressurization process, a pressure fluctuation component due to the pulse wave indicated by the site to be measured from the pressure of the cuff, and thereby detects a one-beat-by-beat waveform pattern. The feature acquisition unit acquires, as the feature information, a one-beat feature amount of the one-beat-by-beat waveform pattern in addition to a direct-current feature amount of the direct-current pressure change pattern. In addition to comparing the acquired direct-current feature amount with the direct-feature feature amount registered in advance, the authentication unit compares the acquired one-beat feature amount with the one-beat feature amount registered in advance, and thereby performs personal authentication on the subject. In this manner, by using the one-beat feature amount as a determination material in addition to the direct-current feature amount, the personal authentication can be performed on the subject with higher accuracy.

In the sphygmomanometer according to one embodiment, the authentication unit does not use the one-beat feature amount but uses only the direct-current feature amount for personal authentication of the subject under a predetermined first condition.

Here, the "predetermined first condition" includes, for example, a condition in which reliability of the one-beat feature amount is low, such as a condition in which the pulse rate at the time of performing the personal authentication is significantly higher or lower than the pulse rate at the time of registering the registered feature information.

In the sphygmomanometer according to this one embodiment, the authentication unit does not use the one-beat feature amount but uses only the direct-current feature amount for personal authentication of the subject under the predetermined first condition. Here, as the first condition, for example, it is assumed that the pulse rate at the time of performing the personal authentication is set to be significantly higher or lower than the pulse rate at the time of registering the registered feature information. According to the sphygmomanometer of this one embodiment, in a case where reliability of the above-described one-beat feature amount is low (that is, in a case where the use of the above-described one-beat feature amount should be excluded), only the above-described direct-current feature amount can be used. As a result, it is possible to prevent the accuracy of the personal authentication from deteriorating.

The sphygmomanometer according to one embodiment further comprises:

a first storage unit; and a feature registration unit that acquires feature information regarding the pressure change pattern of the subject in the pressurization process of the cuff in advance before performing the personal authentication, and performs control to store the acquired feature information in the first storage unit as the registered feature information in association with the subject.

In the sphygmomanometer according to this one embodiment, the feature registration unit performs the following control in advance before performing the personal authentication. First, the feature information regarding the pressure change pattern of the subject is acquired in the pressurization process of the cuff. Next, the acquired feature information is stored in the first storage unit as the registered feature information in association with the subject. As a result, at the stage of performing the personal authentication, the authentication unit can perform the personal authentication on the subject using the registered feature information registered in the first storage unit as a reference for comparison.

The sphygmomanometer according to one embodiment further comprises:

a second storage unit;

a neural network including an input layer, a plurality of intermediate layers, and an output layer each including a plurality of nodes, the neural network having been learned by weighting between each of the nodes, such that, when any one of feature vectors each representing the feature information regarding the pressure change pattern of one of a plurality of teacher users is fed to the input layer, the neural network generates, to the output layer via the plurality of intermediate layers, output information representing a teacher user corresponding to the fed feature information; and a feature registration unit that performs control of:

acquiring, for each user, feature information regarding the pressure change pattern of the user for a user group including the plurality of teacher users and/or users other than the plurality of teacher users in the pressurization process of the cuff in advance before the personal authentication is performed, feeding the acquired feature information to the input layer of the neural network as a feature vector, and storing information appearing in a certain intermediate layer among the plurality of intermediate layers in the second storage unit as the registered feature information in association with the user, wherein, at a stage of performing the personal authentication, the feature acquisition unit acquires feature information regarding the pressure change pattern of the subject to be authenticated in the pressurization process of the cuff, and the authentication unit feeds the acquired feature information as a feature vector to the input layer of the neural network, compares information appearing in the certain intermediate layer among the plurality of intermediate layers with the registered feature information of each user of the user group registered in the second storage unit, and determines whether or not the subject is a user included in the user group.

The "teacher user" refers to a user who has provided the feature information on the pressure change pattern for learning of the neural network. The "user group" includes a plurality of teacher users and/or users other than the teacher users.

In the sphygmomanometer according to this one embodiment, the feature registration unit performs the following control in advance before performing the personal authentication. First, in the pressurization process of the cuff, feature information on the pressure change pattern of the user is acquired for each user for a user group including the plurality of teacher users and/or users other than the teacher users. Next, for each user, the acquired feature information of the user is fed to the input layer of the neural network as a feature vector, and information appearing in a certain intermediate layer among the plurality of intermediate layers is registered in the second storage unit as the registered feature information in association with the user. As a result, the registered feature information is registered in the second storage unit for each user.

In the stage of performing the personal authentication, the feature acquisition unit acquires the feature information on the pressure change pattern of the subject to be authenticated in the pressurization process of the cuff. The authentication unit feeds the acquired feature information of the subject as a feature vector to the input layer of the neural network. Then, the authentication unit compares the information appearing in the certain intermediate layer among the plurality of intermediate layers with the registered feature information of each user of the user group registered in the second storage unit, and determines whether or not the subject is a user included in the user group. As a result, in a case where the subject is a user included in the user group, the subject can be authenticated.

The sphygmomanometer according to one embodiment further comprises an update unit that, when it is determined that the subject is a user registered in advance, updates the registered feature information of the user under a predetermined second condition using the feature information acquired for the subject.

The "predetermined second condition" includes, for example, a condition in which the registered feature information should be updated, such as a fact that a certain period (for example, a period such as one year in which there is a possibility that the feature information about the pressure change pattern changes significantly) has elapsed since a registration of the registered feature information regarding the user (or a previous update).

In the sphygmomanometer according to this one embodiment, when it is determined that the subject is a user registered in advance, the update unit updates the registered feature information of the user under the predetermined second condition using the feature information acquired for the subject. Here, as the second condition, for example, it is assumed that a certain period (for example, a period in which the feature information about the pressure change pattern may significantly change, such as six months.) has elapsed since a registration of the registered feature information of the user (or a previous update). According to the sphygmomanometer of this one embodiment, in a case where such registered feature information is to be updated, the registered feature information can be automatically updated and maintained in an appropriate state. As a result, it is possible to prevent the accuracy of the personal authentication from deteriorating.

In the sphygmomanometer according to one embodiment, the authentication unit cancels the personal authentication under a predetermined third condition.

The "predetermined third condition" includes, for example, a condition in which reliability of the feature information (the direct-current feature amount and/or the one-beat feature amount) about the pressure change pattern is considered to be low, such as a case of detection of an irregular pulse wave.

In the sphygmomanometer according to this one embodiment, the authentication unit cancels the personal authentication under a predetermined third condition. Here, as the third condition, it is assumed that a case of detection of an irregular pulse wave is included, for example. According to the sphygmomanometer of this embodiment, the personal authentication can be canceled when reliability of the feature information (the direct-current feature amount and/or the one-beat feature amount) about the pressure change pattern is low. As a result, it is possible to prevent the accuracy of the personal authentication from deteriorating.

In another aspect, a personal authentication method of the present disclosure is a personal authentication method on a sphygmomanometer including a cuff configured to compress a site to be measured of a subject and measuring a blood pressure by observing a pressure of the cuff, the sphygmomanometer including:

a pressure control unit that performs control to supply a fluid to the cuff to pressurize the cuff or discharge the fluid from the cuff to depressurize the cuff;

a pressure detection unit that detects a pressure of the cuff; and a blood pressure calculation unit that calculates a blood pressure based on an output of the pressure detection unit, the personal authentication method comprising:

acquiring, for a subject to be authenticated, feature information on a pressure change pattern of the cuff with a lapse of time from a start of pressurization in a pressurization process of the cuff; and comparing the acquired feature information with registered feature information on a user registered in advance, and performs personal authentication on the subject.

According to the personal authentication method on a sphygmomanometer of the present disclosure, the personal authentication can be accurately performed with the sphygmomanometer having a simple configuration.

In yet another aspect, a computer-readable recording medium according to the present disclosure is a non-transitorily computer-readable recording medium storing a program for causing a computer to execute the above personal authentication method on a sphygmomanometer.

By making a computer read the program stored in the computer-readable recording medium according to the present disclosure and causing a computer to execute the program, the personal authentication method on a sphygmomanometer can be implemented.

As is clear from the above, according to the sphygmomanometer of the present disclosure, the personal authentication can be accurately performed with a simple configuration. Furthermore, according to the personal authentication method on a sphygmomanometer of the present disclosure, the personal authentication can be accurately performed with the sphygmomanometer having a simple configuration. Furthermore, the personal authentication method on a sphygmomanometer can be implemented by causing a computer to execute the program stored in the computer-readable recording medium of the present disclosure.

The above embodiments are illustrative, and are modifiable in a variety of ways without departing from the scope of this invention. It is to be noted that the various embodiments described above can be appreciated individually within each embodiment, but the embodiments can be combined together. It is also to be noted that the various features in different embodiments can be appreciated individually by its own, but the features in different embodiments can be combined.

The invention claimed is:

1. A sphygmomanometer including a cuff configured to compress a site to be measured of a subject and measuring a blood pressure by observing a pressure of the cuff, the sphygmomanometer comprising:
a pump and a valve each fluidly connected to the cuff;
a pressure sensor that detects a pressure of the cuff; and
a processor, wherein
the processor is configured to act as:
a pressure control unit to perform control, while acquiring the pressure of the cuff from the pressure sensor, so as to supply a fluid from the pump to the cuff to pressurize the cuff or discharge the fluid from the cuff through the valve to depressurize the cuff;
a blood pressure calculation unit to calculate a blood pressure based on the pressure of the cuff;
a feature acquisition unit to acquire, for a subject to be authenticated, feature information regarding a pressure change pattern of the cuff with a lapse of time from a start of pressurization in a pressurization process of the cuff, the feature information including feature information regarding a direct-current pressure change pattern whose increase rate increases over time according to a direct-current component of the pressure of the cuff; and
an authentication unit to perform personal authentication on the subject by comparing the acquired feature information with registered feature information on a user registered in advance.

2. The sphygmomanometer according to claim 1, wherein the processor is configured, when acting as the authentication unit, to:
create a feature amount space having, as coordinate axes, different feature amounts included in the feature information regarding the pressure change pattern,
calculate, in the feature amount space, a point corresponding to the registered feature information for the user registered in advance, and set an allowable range in which the subject is recognized to be the user registered in advance around the point corresponding to the registered feature information; and
determine, in the feature amount space, that the subject is the user registered in advance when a point corresponding to the acquired feature information of the subject falls within the allowable range, and determine that the subject is not the user registered in advance when the point corresponding to the acquired feature information of the subject does not fall within the allowable range.

3. The sphygmomanometer according to claim 1, wherein the processor is further configured to act as:
a first pressure detection unit to extract, in the pressurization process of the cuff, the direct-current component from the pressure of the cuff, and thereby to detect the direct-current pressure change pattern; and
a second pressure detection unit to extract, in the pressurization process of the cuff or a depressurization process subsequent to the pressurization process, a pressure fluctuation component due to a pulse wave indicated by the site to be measured from the pressure of the cuff, and thereby to detect a one-beat-by-beat waveform pattern, and wherein
the processor is configured:
when acting as the feature acquisition unit, to acquire, as the feature information, a one-beat feature amount of the one-beat-by-beat waveform pattern in addition to a direct-current feature amount of the direct-current pressure change pattern, and
when acting as the authentication unit, to perform personal authentication on the subject by comparing the acquired one-beat feature amount with a one-beat feature amount registered in advance, in addition to comparing the acquired direct-current feature amount with a direct-current feature amount registered in advance.

4. The sphygmomanometer according to claim 3, wherein the processor is configured, when acting as the authentication unit, not to use the one-beat feature amount but to use only the direct-current feature amount for personal authentication of the subject under a predetermined first condition.

5. The sphygmomanometer according to claim 1, further comprising:
a memory, wherein
the processor is further configured, in advance before performing the personal authentication, to act as a feature registration unit to acquire feature information regarding the pressure change pattern of the subject in the pressurization process of the cuff, and to perform control to store the acquired feature information in the memory as the registered feature information in association with the subject.

6. The sphygmomanometer according to claim 5, wherein the processor is further configured, when it is determined that the subject is a user registered in advance, to act as an update unit to update the registered feature information of the user under a predetermined second condition using the feature information acquired for the subject.

7. The sphygmomanometer according to claim 1, further comprising:
a memory; and
a neural network including an input layer, a plurality of intermediate layers, and an output layer each including a plurality of nodes, the neural network having been learned by weighting between each of the nodes, such that, when any one of feature vectors each representing the feature information regarding the pressure change pattern of one of a plurality of teacher users is fed to the input layer, the neural network generates, to the output layer via the plurality of intermediate layers, output information representing a teacher user corresponding to the fed feature information, wherein
the processor is further configured, in advance before performing the personal authentication, to act as a feature registration unit to perform control of:
acquiring, for each user, feature information regarding the pressure change pattern of the user for a user group including the plurality of teacher users and/or users other than the plurality of teacher users in the pressurization process of the cuff,
feeding the acquired feature information to the input layer of the neural network as a feature vector, and
storing information appearing in a certain intermediate layer among the plurality of intermediate layers in the memory as the registered feature information in association with the user, and wherein

27 the processor is configured, at a stage of performing the personal authentication:

when acting as the feature acquisition unit, to acquire feature information regarding the pressure change pattern of the subject to be authenticated in the pressurization process of the cuff, and when acting as the authentication unit, to feed the acquired feature information as a feature vector to the input layer of the neural network, to compare information appearing in the certain intermediate layer among the plurality of intermediate layers with the registered feature information of each user of the user group registered in the memory, and to determine whether or not the subject is a user included in the user group.

8. The sphygmomanometer according to claim 1, wherein the processor is configured, when acting as the authentication unit, to cancel the personal authentication under a predetermined third condition.

9. A personal authentication method on the sphygmomanometer according to claim 1,

wherein the personal authentication method is executed by the processor and comprises:

acquiring, for a subject to be authenticated, feature information regarding a pressure change pattern of the cuff with a lapse of time from a start of pressurization in a pressurization process of the cuff, the feature information including feature information regarding a direct-current pressure change pattern whose increase rate increases over time according to a direct-current component of the pressure of the cuff; and performing personal authentication on the subject by comparing the acquired feature information with registered feature information on a user registered in advance.

10. A non-transitory computer-readable recording medium storing a program for causing a computer to execute the personal authentication method on the sphygmomanometer according to claim 9.

* * * * *